(12) United States Patent
Presta et al.

(10) Patent No.: US 8,076,300 B2
(45) Date of Patent: Dec. 13, 2011

(54) FGF2-BINDING PEPTIDES AND USES THEREOF

(75) Inventors: Marco Presta, Brescia (IT); Maura Camozzi, Telgate (IT); Marco Rusnati, Bussero (IT); Maurizio Colombo, San Giorgio-a Cremano (IT); Domenico Mastroianni, Pomigliano D'arco (IT)

(73) Assignee: Tecnogen S.p.A., Piana di Monte Verna (IT)

( * ) Notice: Subject to any disclaimer, the term of this patent is extended or adjusted under 35 U.S.C. 154(b) by 102 days.

(21) Appl. No.: 12/161,950

(22) PCT Filed: Jan. 23, 2007

(86) PCT No.: PCT/EP2007/000538
§ 371 (c)(1),
(2), (4) Date: Dec. 17, 2008

(87) PCT Pub. No.: WO2007/085412
PCT Pub. Date: Aug. 2, 2007

(65) Prior Publication Data
US 2009/0215689 A1     Aug. 27, 2009

(30) Foreign Application Priority Data
Jan. 24, 2006   (EP) ................................. 06001457

(51) Int. Cl.
*A61K 38/18* (2006.01)
*A61K 38/00* (2006.01)
*C07K 14/50* (2006.01)
*C07K 7/00* (2006.01)
*C07K 14/00* (2006.01)

(52) U.S. Cl. ....... 514/21.8; 530/324; 530/327; 530/330; 514/9.1; 514/21.6; 514/21.5; 514/21.3

(58) Field of Classification Search .................... None
See application file for complete search history.

(56) References Cited

U.S. PATENT DOCUMENTS
2008/0015153 A1 * 1/2008 Bottazzi et al. ................ 514/12

FOREIGN PATENT DOCUMENTS
WO   WO 02/38169        5/2002
WO   WO 03/072603   *   9/2003

OTHER PUBLICATIONS

Marco Rusnati et al. "Selective recognition of fibroblast growth factor-2 by the long pentraxin PTX3 inhibits angiogenesis" in Blood, Jul. 1, 2004, vol. 104, No. 1, pp. 92-99, ISSN: 0006-4971.
Marco Rusnati et al. "Fibroblast growth factor/fibroblast growth factor receptor system in angiogenesis" in Cytokine Growth Factor Reviews, Apr. 2005, pp. 159-178, ISSN: 1359-6101.
Catherine Perollet et al. "Platelet factor 4 modulates fibroblast growth factor 2 (FGF-2) activity and inhibits FGF-2 dimerization" in Blood, vol. 91 No. 9, pp. 3289-3299, May 1, 1998, ISSN: 0006-4971.
Maura Camozzi et al. "Pentraxin 3 inhibits fibroblast growth factor 2-dependent activation of smooth muscle cells in vitro and neointima formation in vivo" in Arteriosclerosis, Thrombosis, and Vascular Biology, pp. 1837-1842, Sep. 2005, ISSN: 1524-4636.
Maura Camozzi et al. "Identification of an antiangiogenic FGF-2binding site in the N terminus of the soluble pattern recognition receptor PTX3" in The Journal of Biological Chemistry, pp. 22605-22613, Aug. 11, 2006, ISSN: 0021-9258.

* cited by examiner

*Primary Examiner* — Marianne P Allen
(74) *Attorney, Agent, or Firm* — Steinfl & Bruno LLP

(57) ABSTRACT

FGF2-binding peptides are here described, which have been designed starting from the N-terminal region of PTX3, in particular spanning the PTX3(82-11O) region. Synthetic peptides related to this sequence are able to bind FGF2 and to inhibit its pro-angiogenic activity in vitro and in vivo with no anticipated impact on innate immunity.

4 Claims, 7 Drawing Sheets

SEQUENCE LISTING

```
<160> NUMBER OF SEQ ID NOS: 25

<210> SEQ ID NO 1
<211> LENGTH: 18
<212> TYPE: PRT
<213> ORGANISM: Artificial
<220> FEATURE:
<223> OTHER INFORMATION: synthetic peptide

<400> SEQUENCE: 1

Arg Gly Glu Leu Gln Arg Leu Arg Glu Glu Leu Gly Arg Leu Ala Glu
1               5                   10                  15

Ser Leu

<210> SEQ ID NO 2
<211> LENGTH: 6
<212> TYPE: PRT
<213> ORGANISM: Artificial
<220> FEATURE:
<223> OTHER INFORMATION: synthetic peptide

<400> SEQUENCE: 2

Pro Gly Ala Pro Ala Glu
1               5

<210> SEQ ID NO 3
<211> LENGTH: 3
<212> TYPE: PRT
<213> ORGANISM: Artificial
<220> FEATURE:
<223> OTHER INFORMATION: synthetic peptide

<400> SEQUENCE: 3

Glu Ser Leu
1

<210> SEQ ID NO 4
<211> LENGTH: 3
```

```
<212> TYPE: PRT
<213> ORGANISM: Artificial
<220> FEATURE:
<223> OTHER INFORMATION: synthetic peptide

<400> SEQUENCE: 4

Pro Gly Ala
1

<210> SEQ ID NO 5
<211> LENGTH: 14
<212> TYPE: PRT
<213> ORGANISM: Artificial
<220> FEATURE:
<223> OTHER INFORMATION: synthetic peptide

<400> SEQUENCE: 5

Glu Ser Leu Ala Arg Pro Cys Ala Pro Gly Ala Pro Ala Glu
1               5                   10

<210> SEQ ID NO 6
<211> LENGTH: 11
<212> TYPE: PRT
<213> ORGANISM: Artificial
<220> FEATURE:
<223> OTHER INFORMATION: synthetic peptide

<400> SEQUENCE: 6

Glu Ser Leu Ala Arg Pro Cys Ala Pro Gly Ala
1               5                   10

<210> SEQ ID NO 7
<211> LENGTH: 5
<212> TYPE: PRT
<213> ORGANISM: Artificial
<220> FEATURE:
<223> OTHER INFORMATION: synthetic peptide

<400> SEQUENCE: 7

Ala Arg Pro Cys Ala
1               5

<210> SEQ ID NO 8
<211> LENGTH: 30
<212> TYPE: PRT
<213> ORGANISM: Artificial
<220> FEATURE:
<223> OTHER INFORMATION: synthetic peptide

<400> SEQUENCE: 8

Asp Asn Glu Ile Asp Asn Gly Leu His Pro Thr Glu Asp Pro Thr Pro
1               5                   10                  15

Cys Asp Cys Gly Gln Glu His Ser Glu Trp Asp Lys Leu Phe
                20                  25                  30

<210> SEQ ID NO 9
<211> LENGTH: 29
<212> TYPE: PRT
<213> ORGANISM: Artificial
<220> FEATURE:
<223> OTHER INFORMATION: synthetic peptide

<400> SEQUENCE: 9

Asp Lys Leu Phe Ile Met Leu Glu Asn Ser Gln Met Arg Glu Arg Met
1               5                   10                  15

Leu Leu Gln Ala Thr Asp Val Leu Arg Gly Glu Leu
                20                  25
```

```
<210> SEQ ID NO 10
<211> LENGTH: 29
<212> TYPE: PRT
<213> ORGANISM: Artificial
<220> FEATURE:
<223> OTHER INFORMATION: synthetic peptide

<400> SEQUENCE: 10

Arg Gly Glu Leu Gln Arg Leu Arg Glu Glu Leu Gly Arg Leu Ala Glu
1               5                   10                  15

Ser Leu Ala Arg Pro Cys Ala Pro Gly Ala Pro Ala Glu
            20                  25

<210> SEQ ID NO 11
<211> LENGTH: 29
<212> TYPE: PRT
<213> ORGANISM: Artificial
<220> FEATURE:
<223> OTHER INFORMATION: synthetic peptide

<400> SEQUENCE: 11

Glu Gly Leu Arg Gly Glu Leu Arg Gly Ser Arg Glu Ala Glu Leu Leu
1               5                   10                  15

Arg Gln Ala Ala Arg Ala Pro Ala Cys Pro Leu Pro Glu
            20                  25

<210> SEQ ID NO 12
<211> LENGTH: 26
<212> TYPE: PRT
<213> ORGANISM: Artificial
<220> FEATURE:
<223> OTHER INFORMATION: synthetic peptide

<400> SEQUENCE: 12

Ala Pro Ala Glu Ala Arg Leu Thr Ser Ala Leu Asp Glu Leu Leu Gln
1               5                   10                  15

Ala Thr Arg Asp Ala Gly Arg Arg Leu Ala
            20                  25

<210> SEQ ID NO 13
<211> LENGTH: 15
<212> TYPE: PRT
<213> ORGANISM: Artificial
<220> FEATURE:
<223> OTHER INFORMATION: synthetic peptide

<400> SEQUENCE: 13

Arg Gly Glu Leu Gln Arg Leu Arg Glu Glu Leu Gly Arg Leu Ala
1               5                   10                  15

<210> SEQ ID NO 14
<211> LENGTH: 20
<212> TYPE: PRT
<213> ORGANISM: Artificial
<220> FEATURE:
<223> OTHER INFORMATION: synthetic peptide

<400> SEQUENCE: 14

Arg Gly Glu Leu Gln Arg Leu Arg Glu Glu Leu Gly Arg Leu Ala Glu
1               5                   10                  15

Ser Leu Ala Arg
            20

<210> SEQ ID NO 15
```

```
<211> LENGTH: 8
<212> TYPE: PRT
<213> ORGANISM: Artificial
<220> FEATURE:
<223> OTHER INFORMATION: synthetic peptide

<400> SEQUENCE: 15

Glu Ser Leu Ala Arg Pro Cys Ala
1               5

<210> SEQ ID NO 16
<211> LENGTH: 11
<212> TYPE: PRT
<213> ORGANISM: Artificial
<220> FEATURE:
<223> OTHER INFORMATION: synthetic peptide

<400> SEQUENCE: 16

Ala Arg Pro Cys Ala Pro Gly Ala Pro Ala Glu
1               5                   10

<210> SEQ ID NO 17
<211> LENGTH: 24
<212> TYPE: DNA
<213> ORGANISM: Artificial
<220> FEATURE:
<223> OTHER INFORMATION: primer

<400> SEQUENCE: 17
caccgagaac tcggatgatt atga                                           24

<210> SEQ ID NO 18
<211> LENGTH: 23
<212> TYPE: DNA
<213> ORGANISM: Artificial
<220> FEATURE:
<223> OTHER INFORMATION: synthetic primer

<400> SEQUENCE: 18
ttaacctgcc ggcagccagc tcc                                            23

<210> SEQ ID NO 19
<211> LENGTH: 22
<212> TYPE: DNA
<213> ORGANISM: Artificial
<220> FEATURE:
<223> OTHER INFORMATION: synthetic primer

<400> SEQUENCE: 19
cacctgtgaa acagctattt ta                                             22

<210> SEQ ID NO 20
<211> LENGTH: 21
<212> TYPE: DNA
<213> ORGANISM: Artificial
<220> FEATURE:
<223> OTHER INFORMATION: synthetic primer

<400> SEQUENCE: 20
ttatgaaaca tactgagctc c                                              21

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<222> LOCATION: (1)..(1)
<223> OTHER INFORMATION: Xaa is R1 which is either absent or consists of
      the amino acid sequence selected from SEQ ID NO:1 and SEQ ID NO: 3
<220> FEATURE:
<221> NAME/KEY: MISC_FEATURE
<222> LOCATION: (3)..(3)
<223> OTHER INFORMATION: Xaa is X1 which is an amino acid selected
      between Arg and Lys
<220> FEATURE:
<221> NAME/KEY: MISC_FEATURE
<222> LOCATION: (5)..(5)
<223> OTHER INFORMATION: Xaa is X2 which is an amino acid selected
      between Cys and Thr
<220> FEATURE:
<221> NAME/KEY: MISC_FEATURE
<222> LOCATION: (7)..(7)
<223> OTHER INFORMATION: Xaa is R2 which is either absent or consists of
      the amino acid sequence selected from SEQ ID NO: 2 and SEQ ID NO:4

<400> SEQUENCE: 21

Xaa Ala Xaa Pro Xaa Ala Xaa
1               5

<210> SEQ ID NO 22
<211> LENGTH: 13
<212> TYPE: PRT
<213> ORGANISM: Artificial Sequence
<220> FEATURE:
<223> OTHER INFORMATION: Synthetic peptide

<400> SEQUENCE: 22

His Ile Val Pro Glu Gly Gly Ile Leu Gln Ile Gly Gln
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthetic peptide

<400> SEQUENCE: 23

Pro Glu Gly Gly Ile Leu Gln Ile Gly Gln Glu Lys Asn
1               5                   10

<210> SEQ ID NO 24
<211> LENGTH: 13
<212> TYPE: PRT
<213> ORGANISM: Artificial sequence
<220> FEATURE:
<223> OTHER INFORMATION: Synthetic peptide

<400> SEQUENCE: 24

Gly Ile Leu Gln Ile Gly Gln Glu Lys Asn Gly Ser Ser
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic peptide

<400> SEQUENCE: 25

Arg Leu Arg Glu Glu Leu Gly Arg Leu Ala Glu Ser Leu
1               5                   10
```

FGF2-BINDING PEPTIDES AND USES THEREOF

CROSS REFERENCE TO RELATED APPLICATIONS

This application is the national phase of International Application PCT/EP2007/000538 filed on Jan. 23, 2007 which, in turn, claims priority to European Patent Application 06001457.8 filed on Jan. 24, 2006.

FIELD OF THE INVENTION

The present invention relates to Fibroblast Growth Factor-2 (FGF2)-binding peptides, able to bind FGF2 and to inhibit its pro-angiogenic activity in vitro and in vivo with no anticipated impact on innate immunity.

BACKGROUND OF THE INVENTION

Pentraxins are a superfamily of proteins characterized by a pentameric structure[1]. The classical short-pentraxins C-reactive protein (CRP) and serum amyloid P component (SAP) are acute phase proteins in man and mouse, respectively, produced in liver in response to inflammatory mediators[2,3]. Pentraxins bind various ligands and are involved in the innate resistance to microbes and scavenging of cellular debris and extracellular matrix components[1,4-6].

Long-pentraxins are characterized by an unrelated N-terminal domain coupled to a pentraxin-like C-terminal domain[7]. The prototypic long-pentraxin PTX3[8,9] is a 45 kD glycosylated protein predominantly assembled in 10-20 mer multimers[10]. PTX3 is locally produced and released by different cell types, in particular by mononuclear phagocytes, dendritic cells and endothelial cells, in response to primary inflammatory signals[11]. Studies in ptx3$^{-/-}$ mice have shown that this molecule plays complex non-redundant functions in vivo, ranging from the assembly of a hyaluronic acid-rich extracellular matrix, to female fertility and to innate immunity against diverse microorganisms[12,13]. This is related, at least in part, to the capacity of PTX3 to bind with high affinity the complement component C1q, the extracellular matrix protein TSG6 and selected microorganisms, activating complement activation and facilitating pathogen recognition by macrophages and dendritic cells[1,14]. Thus, PTX3 is a soluble pattern recognition receptor with unique non-redundant functions in various pathophysiological conditions[1,14].

Fibroblast growth factor-2 (FGF2) is a heparin-binding growth factor that induces cell proliferation, chemotaxis, and protease production in cultured endothelial cells by interacting with high affinity tyrosine-kinase receptors (FGFRs)[15]. FGF2 induces angiogenesis in vivo and modulates neovascularization during wound healing, inflammation, atherosclerosis, and tumor growth[16]. Several molecules sequester FGF2 in the extracellular environment, thus preventing its interaction with endothelial cell FGFRs and inhibiting its angiogenic activity (reviewed in[16]). Many of these inhibitors are produced/released locally and/or systemically, thus underlying the complex tuning of the angiogenesis process.

Long PTX3 binds FGF2 with high affinity and specificity. Accordingly, long PTX3 inhibits FGF2-dependent endothelial cell proliferation in vitro and angiogenesis in vivo[17]. Also, whole PTX3 inhibits FGF2-dependent smooth muscle cell activation and intimal thickening after arterial injury[18]. Thus, PTX3 may potentially contribute to the modulation of FGF2 activity in different pathological settings characterized by the co-expression of the two proteins, including inflammation, wound healing, atherosclerosis, and neoplasia. However no therapeutic use of the protein is disclosed given the unfeasibility to utilize such large molecule and to other activities of the protein. As a matter of fact, PTX3 binds C1q via the C-terminal pentraxin domain[10].

At present, no biological functions have been ascribed to the PTX3 N-terminus. On this basis, the authors have investigated the ability of PTX3 N-terminus to interact with FGF2.

DESCRIPTION OF THE INVENTION

It has been found that retroviral transduced endothelial cells over-expressing the PTX3 N-terminal fragment (1-178) show reduced mitogenic activity in response to FGF2. Purified recombinant PTX3(1-178) binds FGF2 and prevents PTX3/FGF2 interaction. Also, the monoclonal antibody mAb-MNB4, that recognizes the PTX3(87-99) epitope, prevents FGF2/PTX3 interaction and abolishes the FGF2 antagonist activity of PTX3. Surprisingly the authors found that very short peptides retain such activity and be useful as therapeutic drugs. Consistently, synthetic peptides PTX3(82-110), PTX3(97-110), PTX3(97-107) and PTX3 (100-104) bind FGF2 and inhibit the interaction of FGF2 with whole long PTX3 immobilized to a BIAcore sensorchip, FGF2-dependent endothelial cell proliferation and angiogenesis in vivo. Thus, the data allow to identify a very short FGF2-binding domain in the N-terminal extension of PTX3 spanning the PTX3(97-110) region. Synthetic peptides related to this sequence are able to bind FGF2 and to inhibit its pro-angiogenic activity in vitro and in vivo with no anticipated impact on innate immunity.

The main object of the present invention is therefore a FGF2-binding peptide of formula I (SEQ ID NO: 21):

R1-Ala-X1-Pro-X2-Ala-R2    (I)

wherein:
X1 is an amino acid selected between Arg and Lys;
X2 is an amino acid selected between Cys and Thr;
R1 is either absent or consists of the amino acid sequence selected from SEQ ID NO: 1 and SEQ 10 NO: 3;
R2 is either absent or consists of the amino acid sequence selected from SEQ ID NO: 2 and SEQ 10 NO: 4, with the following provisions:
when R1 is absent, also R2 is absent; when R1 is the amino acid sequence of SEQ ID NO: 1, R2 is the amino acid sequence of SEQ ID NO: 2; when R1 is the amino acid sequence of SEQ 10 NO: 3, R2 is an amino acid sequence selected between SEQ 10 NO: 2 and SEQ 10 NO: 4; a functional derivative, a precursor or a pharmaceutically acceptable salt thereof.

Preferably, $X_1$ is Arg. More preferably $X_2$ is Cys. Even more preferably the peptide consists of the amino acid sequence selected among SEQ ID NO: 5, SEQ ID NO: 6, SEQ ID NO: 7 and SEQ ID NO: 10.

A further object of the invention is a conjugated chimeric peptide comprising the peptide of formula I or functional derivatives thereof.

The term "peptide" is ordinarily applied to a polypeptidic chain containing from 4 to 100 or more contiguous amino acids, usually from 5 to 20 contiguous amino acids. The term "functional" defines a peptide showing FGF2-binding properties being able to greatly diminish the biological activity of FGF2. The biological activity of FGF2 includes mitogenic and angiogenic effects. In particular, the peptides of the invention are able to inhibit the FGF2-induced proliferation of endothelial cells or smooth muscle cells.

The "precursors" are compounds which can be converted into the compounds of present invention by metabolic and enzymatic processing prior or after the administration to the cells or to the body.

The term "salts" herein refers to both salts of carboxyl groups and to acid addition salts of amino groups of the peptides, polypeptides, or analogs thereof, of the present invention. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Any of such salts should have substantially similar activity to the peptides and polypeptides of the invention or their analogs.

The term "derivatives" as herein used refers to derivatives which can be prepared from the functional groups present on the lateral chains of the amino acid moieties or on the N-/or C-terminal groups according to known methods. Such derivatives include for example esters or aliphatic amides of the carboxyl-groups and N-acyl derivatives of free amino groups or O-acyl derivatives of free hydroxyl-groups and are formed with acyl-groups as for example alcanoyl- or aroyl-groups. The present invention includes also peptidomimetics of the peptides already disclosed, in which the nature of peptides has been chemically modified at the level of amino acid side chains, amino acid chirality, and/or peptide backbone. These alterations are intended to provide FGF2-binding agents having similar (if not improved) therapeutic, diagnostic and/or pharmacokinetic properties.

For example, when the peptide is prone to cleavage by peptidases following injection into the subject, replacement of a particularly sensitive peptide bond with a non-cleavable peptide mimetic can provide a peptide more stable and thus more functional as a therapeutic. Similarly, the replacement of an L-amino acid residue is a standard way of rendering the peptide less sensitive to proteolysis, and finally more similar to organic-compounds other than peptides. Also useful are amino-terminal blocking groups such as t-butyloxycarbonyl, acetyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl. Many other modifications providing increased efficacy, prolonged activity, easiness of purification, and/or increased half-life are known in the art.

The properties of the peptides of the invention can be maintained, or even potentiated, in mutant peptides. Mutant peptides include amino acid sequences wherein one or more amino acid residues have been conservatively substituted, provided they display the same biological activity characterizing the present invention at equivalent or even higher levels, as determined by means known in the art or disclosed in the Examples below.

In accordance with the present invention, preferred changes in the mutant peptides are commonly known as "conservative" or "safe" substitutions. Conservative amino acid substitutions are those with amino acids having sufficiently similar chemical properties, in order to preserve the structure and the biological function of the molecule. The literature provides many models on which the selection of conservative amino acids substitutions can be performed on the basis of statistical and physico-chemical studies on the sequence and/or the structure of natural protein.

Mutant peptides may result from conventional site-directed mutagenesis technique of the encoding DNA, from combinatorial technologies at the level of encoding DNA sequence (such as DNA shuffling, phage display/selection) or of amino acids, from computer-aided design studies, or any other known technique suitable thereof, which afford a finite set of substantially corresponding mutated peptides which can be routinely obtained and tested by one of ordinary skill in the art using the teachings presented in the prior art and in the Examples of the present patent application.

Another object of the invention is a fused chimeric peptide comprising the peptide of formula (I) or functional derivatives thereof. The FGF2-binding peptides being fusion and/or chimeric peptides comprise the amino acid sequence of the peptide of Formula (I) or any of their mutants/derivatives as defined above, and an amino acid sequence belonging to a protein sequence other than PTX3, providing additional properties without considerably impairing FGF2-binding activity.

Additional protein sequences which can be comprised in fusion and/or chimeric proteins can be chosen amongst membrane-bound sequences, extracellular regions of membrane-bound proteins, immunoglobulin constant regions, multimerization domains, extracellular proteins, signal peptide-containing proteins, export signal-containing proteins.

The additional properties displayed by the fusion and/or chimeric polypeptides or peptides are an easier purification capacity, a longer lasting half-life in body fluids, or extracellular localization. This latter feature is of particular importance for defining a specific group of fusion or chimeric proteins included in the above definition since it allows the peptides of the invention to be localized in the space where not only the isolation and purification of these peptides is facilitated, but also where PTX3 and FGF2 naturally interact.

The choice of one or more of the sequences to be fused to the FGF2-binding peptide depends on specific use of said peptide.

As a general procedure, fusion proteins can be produced by generating nucleic acid segments encoding them, using common genetic engineering techniques, and cloning in replicable vector of viral or plasmid origin which are used to modify a Prokaryotic or Eukaryotic host cell, using episomal or non-/homologously integrated vectors, as well as transformation-, infection-, or transfection-based technologies. These vectors should allow the expression of the fusion protein including the FGF2-binding agent in the prokaryotic or eukaryotic host cell under the control of their own transcriptional initiation/termination regulatory sequences, which are chosen to be constitutively active or inducible in said cell. A cell line can be then isolated to provide a stable cell line. In particular, whenever cells modified to express the FGF2-binding agents of the invention are directly used or administered, preferred cells are human cells, normally expressing PTX3. When the additional protein sequence, as in the case of the sequence of extracellular, export signal, or signal-peptide containing proteins, allows the FGF2-binding domain to be secreted in the extracellular space, the agent can be more easily collected and purified from cultured cells in view of further processing or, alternatively, the cells can be directly used or administered.

When the additional protein, as in the case of the sequence of membrane-bound proteins, allows the immobilization of the FGF2-binding agent on the surface of the cell, the agent can be less easily collected and purified from the cultured cells in view of further processing but the cells can be directly used or administered providing the agent in a form corresponding to the one of natural PTX3, possibly improving its properties.

The FGF2-binding peptides of the invention can be identified also by methods of computer-aided drug design which make use of the structure and/or sequence of the peptides of the invention, or the corresponding active mutants as defined above. The peptides of the invention may be used to study the interaction between PTX3 and FGF2 with greater efficacy using computational modelling technologies. Such computer-assisted analysis can be exploited to develop improved peptide or non-peptide mimetic drugs in the form of synthetic organic molecules or peptides (for example, 4-20 amino acids long). Once that these compounds have been screened and found to be capable of binding FGF2, their use will then be assessed using cell or animal models.

The polypeptides of the invention can be in the form of active conjugates or complex with a heterologous moiety, which may be selected from cytotoxic agents, labels (e.g. biotin, fluorescent labels), drugs or other therapeutic agents, covalently bound or not, either directly or through the use of coupling agents or linkers. Useful conjugates or complexes can be generated using molecules and methods known in the art (radioactive or fluorescent labels, biotin, cytotoxic agents, drugs or other therapeutic agents). Cytotoxic agents include chemotherapeutic agents, toxin (e.g., an enzymatically active toxin of bacterial, fungal, plant, or animal origin, or fragments thereof), or a radioactive isotope (i.e., a radioconjugate). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes. A variety of radionuclides are available for the production of radioconjugated proteins. Examples include $^{212}Bi$, $^{131}I$, $^{131}In$, $^{90}Y$, and $^{186}Re$.

Useful conjugates or complexes can also be generated for improving the agents in terms of drug delivery efficacy. For this purpose, the peptides of the invention can be in the form of active conjugates or complex with molecules such as polyethylene glycol and other natural or synthetic polymers (Harris J M and Chess R B, Nat Rev Drug Discov. (2003), 2(3): 214-21; Greenwald R B et al., Adv Drug Deliv Rev. (2003), 55(2):217-50; Pillai 0 and Panchagnula R, Curr Opin Chem. Biol. (2001), 5(4):447-51). In this regard, the present invention contemplates chemically modified peptides as disclosed herein, in which the peptide is linked with a polymer. Typically, the polymer is water soluble so that the conjugate does not precipitate in an aqueous environment, such as a physiological environment. The conjugates used for therapy can comprise pharmaceutically acceptable water-soluble polymer moieties. Suitable water-soluble polymers include polyethylene glycol (PEG), monomethoxy-PEG, mono-(Cl— C10) alkoxy-PEG, aryloxy-PEG, poly-(N-vinyl pyrrolidone) PEG, tresyl monomethoxy PEG, PEG propionaldehyde, bis-succinimidyl carbonate PEG, propylene glycol homopolymers, a polypropyleneoxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A conjugate can also comprise a mixture of such water-soluble polymers.

Examples of conjugates comprise the peptides of the invention and a polyallyl oxide moiety attached to the N-terminus of said polypeptide moiety. PEG is one suitable polyalkyl oxide. As an illustration, the peptides of the present invention can be modified with PEG, a process known as "PEGylation." PEGylation can be carried out by any of the PEGylation reactions known in the art. For example, PEGylation can be performed by an acylation reaction or by an alkylation reaction with a reactive polyethylene glycol molecule. In an alternative approach, conjugates are formed by condensing activated PEG, in which a terminal hydroxy or amino group of PEG has been replaced by an activated linker.

Another object of the invention is represented by a nucleic acids encoding the FGF2-binding peptides of the invention, nucleic acids hybridizing with the above nucleic acids, nucleic acids having degenerated sequences.

The invention also includes expression vectors of viral or plasmid origin which allows the expression of the nucleic acid of the invention and prokaryotic or eukaryotic host cells transformed with such vectors and stable cell lines derived therefrom, expressing the FGF2-binding agent, which can be secreted or expressed on the membrane surface. Examples are human B cells.

FGF2-binding peptides of the invention can be produced by method wherein the host cells above described, are cultured in an appropriate culture media and the FGF2-binding agent is collected.

The DNA sequence coding for the peptides of the invention can be inserted and ligated into a suitable vector. Once formed, the expression vector is introduced into a suitable host cell, which then expresses the peptide.

Expression of any of the recombinant peptides of the invention as mentioned herein can be effected in eukaryotic cells (e.g. yeasts, insect or mammalian cells) or prokaryotic cells, using the appropriate expression vectors. Any method known in the art can be employed.

In order to be capable of expressing the desired protein, an expression vector should also comprise specific nucleotide sequences containing transcriptional and translational regulatory information linked to the DNA coding the desired protein in such a way as to permit gene expression and production of the protein. First in order for the gene to be transcribed, it must be preceded by a promoter recognizable by RNA polymerase, to which the polymerase binds and thus initiates the transcription process.

There are a variety of such promoters in use, which work with different efficiencies (strong and weak promoters).

For eukaryotic hosts, different transcriptional and translational regulatory sequences may be employed, depending on the nature of the host. They may be derived form viral sources, such as adenovirus, bovine papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated.

The DNA molecule comprising the nucleotide sequence coding for the protein of the invention is inserted into vector (s), having the operably linked transcriptional and translational regulatory signals, which is capable of integrating the desired gene sequences into the host cell.

The cells that have been stably transformed by the introduced DNA can be selected by also introducing one or more markers allowing for selection of host cells containing the expression vector. The marker may also provide for phototrophy to an auxotropic host, biocide resistance, e.g. antibiotics, or heavy metals such as copper, or the like. The selectable marker gene can either be directly linked to the DNA gene sequences to be expressed, or introduced into the same cell by co-transfection.

Additional elements of the vectors may also be useful for obtaining an optimal production of proteins of the invention, in particular for selecting a particular cell containing plasmid or viral vector: the ease with which recipient cells, that contain the vector may be recognized and selected from those recipient cells which do not contain the vector; the number of copies of the vector which are desired in a particular host; and whether it is desirable to be able to "shuttle" the vector between host cells of different species.

Once the vector(s) or DNA sequence containing the construct(s) has been prepared for expression the DNA constructs) may be introduced into an appropriate host cell by any of a variety of suitable means: transformation, transfection, conjugation, protoplast fusion, electroporation, calcium phosphate-precipitation, direct microinjection, etc.

Host cells may be either prokaryotic or eukaryotic. Preferred are eukaryotic hosts, e.g. mammalian cells, such as human, monkey, mouse, and Chinese Hamster Ovary (CHO) cells, because they provide post-translational modifications to protein molecules, including correct folding or glycosylation at correct sites. Also yeast cells can carry out post-translational peptide modifications including glycosylation. A number of recombinant DNA strategies exist which utilize strong promoter sequences and high copy number of plasmids that can be utilized for production of the desired proteins in yeast. Yeast recognizes leader sequences on cloned mammalian gene products and secretes peptides bearing leader sequences (i.e., pre-peptides).

After the introduction of the vector(s), the host cells are grown in a selective medium, which selects for the growth of vector-containing cells. Expression of the cloned gene sequence (s) results in the production of the desired proteins.

Many reviews and books provides teachings on how to clone and produce recombinant proteins using vectors and Prokaryotic or Eukaryotic host cells, such as some titles in the series "A Practical Approach" published by Oxford University Press ("DNA Cloning 2: Expression Systems", 1995; "DNA Cloning 4: Mammalian Systems", 1996; "Protein Expression", 1999; "Protein Purification Techniques", 2001).

Examples of chemical synthesis technologies, which are more indicated for producing the FGF2-binding agent of the invention when they are in the form of peptide or peptide mimetics, are solid phase synthesis and liquid phase synthesis. As a solid phase synthesis, for example, the amino acid corresponding to the C-terminus of the peptide to be synthetized is bound to a support which is insoluble in organic solvents, and by alternate repetition of reactions, one wherein amino acids with their amino groups and side chain functional groups protected with appropriate protective groups are condensed one by one in order from the C-terminus to the N-terminus, and one where the amino acids bound to the resin or the protective group of the amino groups of the peptides are released, the peptide chain is thus extended in this manner.

Solid phase synthesis methods are largely classified by the tBoc method and the Fmoc method, depending on the type of protective group used. Typically used protective groups include tBoc (t-butoxycarbonyl), Cl—Z (2-chlorobenzyloxycarbonyl), Br—Z (2-bromobenzyloxycarbonyl), Bzl (benzyl), Fmoc (9-fluorenylmethoxycarbonyl), Mbh (4,4'-dimethoxydibenzhydryl), Mtr (4-methoxy-2,3,6-trimethylbenzenesulphonyl), Trt (trityl), Tos(tosyl), Z (benzyloxycarbonyl) and $Cl_2$-Bzl (2,6-dichlorobenzyl) for the amino groups; $NO_2$ (nitro) and Pmc (2,2,5,7,8-pentamethylchromane-6-sulphonyl) for the guanidino groups); and tBu (t-butyl) for the hydroxyl groups). After synthesis of the desired peptide, it is subjected to the de-protection reaction and cut out from the solid support. Such peptide cutting reaction may be carried with hydrogen fluoride or tri-fluoromethane sulfonic acid for the Boc method, and with TFA for the Fmoc method.

The FGF2-binding agents obtained by recombinant DNA or chemical synthesis technologies are finally subjected to one or more steps of purification. Purification can be carried out by any one of the methods known for this purpose, i.e. any conventional procedure involving extraction, precipitation, chromatography, electrophoresis, or the like. For example, HPLC (High Performance Liquid Chromatography) can be used. The elution can be carried using a water-acetonitrile-based solvent commonly employed for protein purification. The invention includes purified preparations of the FGF2-binding agents of the invention. Purified preparations, as used herein, refers to the preparations which are at least 1%, preferably at least 5%, by dry weight of the compounds of the invention.

The compounds of the invention described above (proteins, peptides, organic compounds) can be used as a medicament. Preferably as an anti-disease brought about by an altered angiogenesis. More preferably the altered angiogenesis is provoked by an altered activation of the growth factor FGF2. Even more preferably the disease is selected from the group consisting of arthritic disease, tumor metastasis, diabetic retinopathy, psoriasis, chronic inflammation, arteriosclerosis or tumor. Preferably the tumor is selected from the group of: sarcoma, carcinoma, carcinoid, bone tumor or neuroendocrine tumor.

The compounds of the invention described above (proteins, peptides, organic compounds) can be used as anti-disease associated with uncontrolled FGF2-dependent proliferation of fibroblasts or smooth muscular cells, cicatrization linked to excessive fibroblastic response, and restenosis after angioplastic.

As a matter of fact the FGF2-binding peptides of the invention, once bound to FGF2, acts as inhibitor of FGF2. Indeed the peptides are able to inhibit the FGF2-induced proliferation of endothelial cells or smooth muscle cells. Therefore the therapeutic potential of such molecule is the prophylaxis and/or treatment of diseases in which an inhibition of FGF2 is beneficial. This latter effect can be also used for reducing the population of cells that express FGF2.

The FGF2-binding peptides of the invention can be used as active ingredients in pharmaceutical compositions for the prophylaxis and/or treatment of diseases brought about by an altered angiogenesis, in which the altered angiogenesis is provoked by an altered activation of FGF2. Example of said diseases are: arthritic disease, tumor metastasis, diabetic retinopathy, psoriasis, chronic inflammation, arteriosclerosis or tumor, in which the tumor is, for example, sarcoma, carcinoma, carcinoid, bone tumor or neuroendocrine tumor.

The FGF2-binding agents of the invention can also be used as active ingredients in pharmaceutical compositions for the prophylaxis and/or treatment of diseases associated with uncontrolled FGF2-dependent proliferation of fibroblasts or smooth muscular cells, such as the cicatrization linked to excessive fibroblastic response, and the restenosis after angioplastic.

The present invention also provides pharmaceutical composition comprising a therapeutically effective amount of the peptide of formula I or functional derivatives thereof and suitable diluents and/or excipients and/or adjuvants pharmaceutical for the prophylaxis and/or treatment of the above-mentioned diseases. These pharmaceutical compositions can be formulated in combination with pharmaceutically acceptable carriers, excipients, stabilizers, or diluents. Depending on the properties of the agent, the pharmaceutical composition can be useful for diseases related to CD4+ T cells such as autoimmune diseases, inflammations, or infections.

Pharmaceutical compositions comprising the FGF2-binding peptides of the present invention include all compositions wherein said compound is contained in therapeutically effective amount, that is, an amount effective to achieve the medically desirable result in the treated animal. The pharmaceutical compositions may contain suitable pharmaceutical acceptable carriers, biologically compatible vehicles suitable for administration to an animal (for example, physiological saline) and eventually comprising auxiliaries (like excipients, stabilizers or diluents) which facilitate the processing of the active compounds into preparations which can be used pharmaceutical.

The pharmaceutical compositions may be formulated in any acceptable way to meet the needs of the mode of administration. The use of biomaterials and other polymers for drug delivery, as well the different techniques and models to validate a specific mode of administration, are disclosed in literature. Modifications of the compounds of the invention to improve penetration of the blood-brain barrier would also be useful.

Any accepted mode of administration can be used and determined by those skilled in the art. For example, administration may be by various parenteral routes such as subcutaneous, intravenous, intradermal, intramuscular, intraperitoneal, intranasal, transdermal, oral, or buccal routes. Parenteral administration can be by bolus injection or by gradual perfusion over time. Preparations for parenteral administration include sterile aqueous or non-aqueous solutions, suspensions, and emulsions, which may contain auxiliary agents or excipients known in the art, and can be prepared according to routine methods. In addition, suspension of the active compounds as appropriate oily injection suspensions may be administered. Suitable lipophilic solvents or vehicles include fatty oils, for example, sesame oil, or synthetic fatty acid esters, for example, sesame oil, or synthetic fatty acid esters, for example, ethyloleate or triglycerides.

Aqueous injection suspensions that may contain substances increasing the viscosity of the suspension include, for example, sodium carboxymethyl cellulose, sorbitol, and/or dextran. Optionally, the suspension may also contain stabilizers. Pharmaceutical compositions include suitable solutions for administration by injection, and contain from about 0.01 to 99 percent, preferably from about 20 to 75 percent of active compound together with the excipient. Compositions which can be administered rectally include suppositories.

It is understood that the dosage administered will be dependent upon the age, sex, health, and weight of the recipient, kind of concurrent treatment, if any, frequency of treatment, and the nature of the effect desired. The dosage will be tailored to the individual subject, as is understood and determinable by one of skill in the art. The total dose required for each treatment may be administered by multiple doses or in a single dose. The pharmaceutical composition of the present invention may be administered alone or in conjunction with other therapeutics directed to the condition, or directed to other symptoms of the condition. Usually a daily dosage of active ingredient is comprised between 0.01 to 100 milligrams per kilogram of body weight.

The compounds of the present invention may be administered to the patient intravenously in a pharmaceutical acceptable carrier such as physiological saline. Standard methods for intracellular delivery of peptides can be used, e.g. delivery via liposomes. Such methods are well known to those of ordinary skill in the art. The formulations of this invention are useful for parenteral administration, such as intravenous, subcutaneous, intramuscular, and intraperitoneal.

As well known in the medical arts, dosages for any one patient depends upon many factors, including the patient's size, body surface area, age, the particular compound to be administered, sex, time and route of administration, general health, and other drugs being administered concurrently.

All references cited herein are entirely incorporated by reference herein, including all data, tables, figures, and text presented in the cited references. Additionally, the entire contents of the references cited within the references cited herein are also entirely incorporated by reference. Reference to known method steps, conventional method steps, known methods or conventional methods is not in any way an admission that any aspect, description or embodiment of the present invention is disclosed, taught or suggested in the relevant art.

Once understood the features of the methods and products disclosed in present application, the necessity and kind of additional steps can be easily deduced by reviewing prior art, as well as the non-limiting following figures and examples describing the basic details and some applications of the invention

EXAMPLES

Example 1

Materials and Methods

Chemicals

Figure 1:
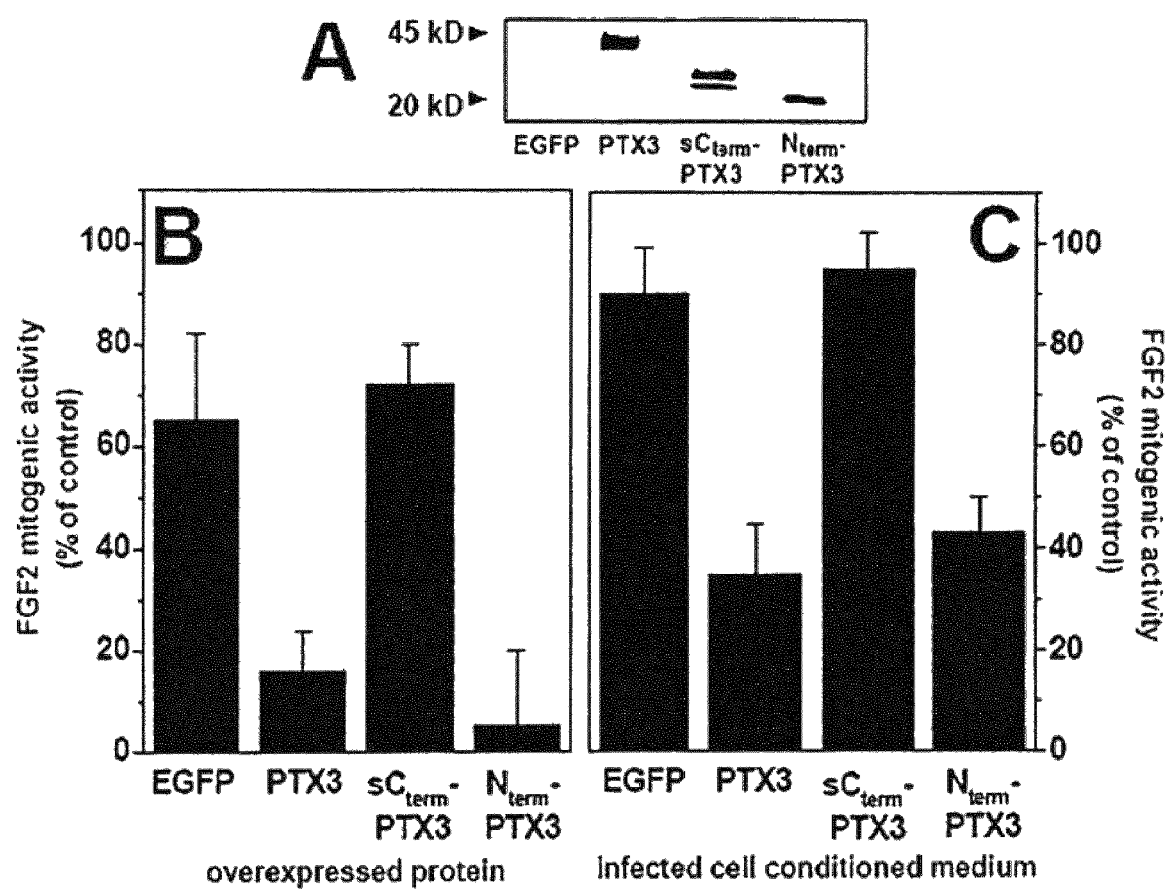
FIG. 1. Inhibition of FGF2 mitogenic activity by retrovirus transduced $N_{term}$-PTX3. (A) Western blot analysis of the conditioned medium of murine aortic endothelial (MAE) cells infected with EGFP, human full length PTX3, $sC_{term}$-PTX3, or $N_{term}$-PTX3 retroviruses. The two immunoreactive bands present in the $sC_{term}$-PTX3 lane correspond to the glycosylated and non-glycosilated form of the recombinant protein[10]. (B) Retrovirus infected MAE cells were stimulated with FGF2 (0.55 nM). After 48 h, cells were trypsinized and counted. Data are expressed as percentage of the proliferation observed in mock-infected FGF2-treated cells (0.8 cell population doublings). (C) GM7373 cells were incubated with the conditioned medium from infected MAE cells and immediately treated with 0.55 nM FGF2. After 24 h, cells were trypsinized and counted. Data are expressed as percentage of the proliferation observed in GM7373 cells incubated in fresh medium plus FGF2 (1.0 cell population doublings). In B and C, data are the mean±SD of 3 independent experiments in triplicate.

Human recombinant FGF2 (accession number 09038) and PTX3 (accession number swiss-prot P26022) were expressed in *E. coli* and Chinese hamster ovary cells, respectively, and purified as described 10,19. Synthetic human PTX3(31-60), PTX3(57-85), and PTX3(107-132) peptides were provided by Primm (Milan, Italy), all the other peptides being provided by Tecnogen (Piana di Monteverna, Caserta, Italy) (HPLC purity≧95%). For all peptides, amino acid sequence is shown in Table 1 in the single letter code and numbering stars from the methionine residue in position 1 in the PTX3 leader sequence.

TABLE 1

Synthetic peptides spanning the human PTX3 N-terminus.

| Peptide | Amino acid sequence | SEQ ID NO: |
| --- | --- | --- |
| PTX3(31-60) | DNEIDNGLHPTEDPTPCDCGQEHSEWDKLF | 8 |
| PTX3(57-85) | DKLFIMLENSQMRERMLLQATDDVLRGEL | 9 |
| PTX3(82-110) | RGELQRLREELGRLAESLARPCAPGAPAE | 10 |
| Scrambled PTX3(82-110) | EGLRGELRGSREAELLRQAARAPACPLPE | 11 |
| PTX3(107-132) | APAEARLTSALDELLQATRDAGRRLA | 12 |
| PTX3(82-96) | RGELQRLREELGRLA | 13 |
| PTX3(82-101) | RGELQRLREELGRLAESLAR | 14 |
| PTX3(97-110) | ESLARPCAPGAPAE | 5 |
| PTX3(97-104) | ESLARPCA | 15 |
| PTX3(97-107) | ESLARPCAPGA | 6 |
| PTX3(100-104) | ARPCA | 7 |
| PTX3(100-110) | ARPCAPGAPAE | 16 |
| PTX3(82-99) | RGELQRLREELGRLAESL | 1 |
| PTX3(105-110) | PGAPAE | 2 |
| PTX3(97-99) | ESL | 3 |
| PTX3(105-107) | PGA | 4 |

Rat monoclonal antibodies directed against purified human PTX3 were described previously[10,20] (MNB1 cat. Number ALX-804-463, MNB4 cat. Number ALX-804-464, Alexis Biochemicals).

Cell Cultures

Fetal bovine aortic endothelial GM7373 cells[21] were grown in Eagle's MEM containing 10% fetal calf serum (FCS). Human embryonic kidney (EcoPack2-293) packaging cells (Clontech, Calif., USA) were grown in DMEM (Life Technologies, Gaithersburg, Md.) containing 10% FCS.

Balb/c murine aortic endothelial 22106 cells (MAE cells) were obtained from R. Auerbach (University of Wisconsin, Madison, Wis.) and grown in DMEM added with 10% FCS.

Retroviral Infection

The cDNAs encoding for human PTX3 and for the enhanced green fluorescent protein (EGFP) were obtained as described[17]. The cDNAs encoding for the N-terminal fragment PTX3(1-178) ($N_{term}$-PTX3) and the C-terminal fragment PTX3(179-381) fused to the leader sequence for secretion PTX3(1-17) ($sC_{term}$-PTX3) were generated from pLX-PTX3[17] by PCR and standard cloning techniques. All cDNAs were cloned in the pBABE retroviral vector thus generating pBABE-PTX3, pBABE-$N_{term}$-PTX3, pBABE-$sC_{term}$-PTX3, and pBABE-EGFP that were used to transfect the EcoPack2-293 packaging cells in the presence of Lipofectamin 17. Transduced cells were selected with puromycin (1 µg/ml, Sigma) for 2 weeks. Clones with a viral titer higher than 106 cfu/mL were used for further experimentation. Confluent cultures of MAE cells were then incubated for 24 hours with the conditioned medium from pBABE-PTX3, pBABE-$N_{term}$-PTX3, PBABE-$sC_{term}$-PTX3, or pBABE-EGFP packaging cells in the presence of polybrene (8 µg/ml, Sigma). Infected cell populations were selected for 7 days with puromycin. Observation of EGFP-infected cells by epifluorescence microscopy (Axiovert S100 microscope, ×10/0.25; Zeiss, Gottingen, Germany) showed that retroviral infection efficiency was higher than 80%. To assess the levels of transgene protein expression and release by infected cells, cell cultures were grown under serum-free conditions for 2 days. Then, conditioned media were collected, clarified by centrifugation, concentrated 10-fold using Centricon YM-10 filters (Millipore), and 100 µl aliquots were probed by Western blot analysis.

Cell Proliferation Assay

Cell proliferation assay on endothelial cells was performed as described[22]. Briefly, GM7373 or MAE cells were seeded in 96-well dishes at 75,000 cells/cm² or 25,000 cells/cm², respectively. After 16 h, cells were incubated in fresh medium containing 0.4% FCS plus FGF2 (0.55 nM) in the absence or in the presence of different antagonists. After 24 or 48 h, respectively, cells were trypsinized and counted in a Burker chamber.

E. coli Expression and Purification of Recombinant 6×His-tagged PTX3 Fragments $N_{term}$-PTX3 and $C_{term}$-PTX3 cDNAs were amplified from pLX-PTX3 by PCR with primers containing additional nucleotides

```
PTX3-N:
(+) CACCGAGAACTCGGATGATTATGA 8;    (SEQ ID 17)
(-) TTAACCTGCCGGCAGCCAGCTCC;       (SEQ ID 18)

PTX3-C:
(+) CACCTGTGAAACAGCTATTTTA;        (SEQ ID 19)
(-) TTATGAAACATACTGAGCTCC.         (SEQ ID 20)
```

These cDNAs were cloned into the PENTR TOPO vector (PENTR Directional TOPO Cloning Kit, Invitrogen) and sequenced. By using the Gateway© technology (Invitrogen), $N_{term}$-PTX3 and $C_{term}$-PTX3 cDNAs from pENTR TOPO vector were then cloned into the pDEST17 vector allowing the insertion of a 6×His-tag at the C-terminus of the recombinant proteins. E. coli BL21-AI cells (Invitrogen) were then transformed with the two recombinant plasmids and grown at 37° C. in LB medium containing 100 µg/mL ampicillin. Recombinant protein expression was induced by overnight incubation at 30° C. in the presence of 0.2% L-arabinose. After induction, cells were resuspended in binding buffer (20 mM sodium phosphate, 0.5 M NaCl, 10 mM imidazole, pH 7.4) and lysed by sonication. Clarified supernatants were filtered through a 0.45 µm filter and loaded onto a 3.0 ml HiTrap Immobilized Metal Affinity Column (IMAC) (Amersham Biosciences) with Nickel for purification. The column was washed with 100 mM imidazole in binding buffer and bound proteins were eluted with 300 mM imidazole according to manufacturer's instructions. Fractions were probed for the presence of the recombinant protein by immunoblotting, and positive fractions were collected and desalted by gel filtration chromatography (Sephadex G25 column PD10, Amersham) in PBS. Purity of recombinant proteins was higher than 90%, as assessed by SDS-PAGE followed by silver staining of the gel (see FIG. 2A, inset).

Solid Phase Binding Assay

ELISA microplates were incubated for 16 hours at 4° C. with 100 µl/well of 100 mM NaHCO₃, pH 9.6 (coating buffer) containing FGF2 (270 nM). Then, wells were overcoated for 2 hours at room temperature with 5% dry milk in coating buffer. Next, 100 µl aliquots of PBS containing full length PTX3, recombinant $N_{term}$-PTX3 or $C_{term}$-PTX3 (all at 44 nM) were incubated for 30 minutes at 37° C. onto the FGF2-coated wells. Then, wells were sequentially incubated for 1 hour at 37° C. with a rabbit polyclonal anti-PTX3 antibody (1:2000 dilution) that recognizes both PTX3 fragments with similar efficiency in Western blot and ELISA, an anti-rabbit biotinylated antibody (1:2000), and 100 µl of streptavidin-horseredish peroxidase (1:5000, Amersham) for 1 hour at room temperature. Then, 100 µl/well of the chromogen substrate 2,29-azinobis(3-ethylbenzthiazolinesulfonic acid) were added. Absorbance values were read at 405 nm in an automatic ELISA reader. In some experiments, 100-µl aliquots of PBS containing biotin-labeled PTX3 (bPTX3) (22 nM) were incubated for 30 minutes at 37° C. onto FGF2-coated wells with or without competitors. Then, wells were washed, and the amount of bound bPTX3 was evaluated as described[17]. Alternatively, synthetic PTX3 peptides were immobilized on ELISA microplate wells (200 µg/well) as described above. Then, FGF2 (80 nM) was added and FGF2 bound to immobilized peptides was assessed by 1 hour incubation at 37° C. with a rabbit polyclonal anti-FGF2 antibody (1:7000) followed by immunocomplex detection as described above.

PTX3 Epitope Mapping

To identify the amino acid sequence of the epitopes binding to monoclonal anti-PTX3 antibodies, 128 peptides were arrayed onto cellulose membranes by SPOT-synthesis technology[23]. The peptides were 13-amino acid long with a 3-amino acid frameshift. Membranes were blocked with 2% milk in Tween-TBS (MBS) for 16 hours at 4° C. After washing, the membranes were incubated for 90 minutes at 37° C. with monoclonal antibodies mAb MNB4 or mAb 16B5 (both at 1:1000 dilution in MBS) and then incubated for 90 minutes at 37° C. with rabbit alkaline phosphatase-conjugated anti-rat IgG (1:30,000, Sigma) in MBS. Color reaction was developed as described 23 and intensity of the signal was evaluated by densitometric analysis of the membrane.

BIAcore Binding Assay

A BIAcore X apparatus (BIAcore Inc, Piscataway, N.J.) was used. Surface plasmon resonance was exploited to measure changes in refractive index caused by the ability of FGF2 to bind to PTX3 immobilized to a BIAcore sensorchip. To this purpose, PTX3 (2.2 µM) was allowed to react with a flow cell of a CM4 sensorchip that was previously activated with 50 µl of a mixture of 0.2 M N-ethyl-N'-(3-dimethylaminopropyl)-carbodiimide hydrochloride and 0.05 M N-hydroxysuccinimide. These experimental conditions allowed the immobilization of 5,000 resonance units (RUs), corresponding to approximately 0.1 pmoles of PTX3. Similar results were obtained for immobilization of gelatin, here used as a negative control and for blank subtraction. Increasing concentrations of FGF2 with or without synthetic PTX3 peptides were then injected in dilution buffer (PBS plus 0.005% surfactant P20, 5.0 µg/mL CaCl$_2$ and MgCl$_2$) over the PTX3 surface for 4 minutes (to allow their association with immobilized PTX3) and then washed until dissociation was observed.

Chicken Embryo Chorioallantoic Membrane (CAM) Assay

Alginate beads (5 µl) containing vehicle or 16 pmoles of FGF2 with or without synthetic PTX3 peptides were prepared as described 24 and placed on top of the CAM of fertilized White Leghorn chicken eggs at day 11 of incubation (10 eggs per experimental group). After 72 hours, blood vessels converging towards the implant were counted by two observers in a double-blind fashion under a stereomicroscope (STEMI-SR, x2/0.12; Zeiss).

Results

The N-terminal Region of PTX3 Binds FGF2

PTX3 protein is characterized by a C-terminal 203-amino acid domain ($C_{term}$-PTX3) that shares homology with the classic short-pentraxins CRP and SAP and by an N-terminal 178-amino acid extension ($N_{term}$-PTX3) that does not show any significant homology with any other known protein 8. In the attempt to identify the antiangiogenic, FGF2-binding domain(s) of PTX3, the two $C_{term}$ or $N_{term}$-PTX3 portions were assessed for their capacity to interact with FGF2.

Previous observations had shown that the overexpression of full length PTX3 results in the inhibition of FGF2-dependent proliferation in endothelial cells due to the binding of released PTX3 to the exogenous growth factor and its sequestration in the extracellular milieu 17. On this basis, murine aortic endothelial (MAE) cells were infected with retroviruses harboring human full length PTX3, the PTX3 N-terminal extension $N_{term}$-PTX3, or the PTX3 C-terminus fused to the PTX3 leader sequence for secretion (s$C_{term}$-PTX3). Control cells were infected with an EGFP-harboring retrovirus. Infected cells overexpressed and released the corresponding proteins in similar amounts (FIG. 1A) and showed a similar rate of growth under basal conditions. However, $N_{term}$-PTX3 overexpression caused a significant decrease in the capacity of infected cells to proliferate in response to exogenous FGF2, similar to full length PTX3-overexpression (FIG. 1B). No inhibition was instead exerted by s$C_{term}$-PTX$^3$ overexpression when compared to control EGFP-infected cells.

To further assess the capacity of $N_{term}$-PTX3 to act as a FGF2-antagonist, conditioned media of infected MAE cells were evaluated for the capacity to affect FGF2-dependent proliferation of endothelial GM7373 cells (FIG. 1C). As anticipated, incubation of GM7373 cells with FGF2 in the presence of the conditioned medium of $N_{term}$-PTX3-infected or PTX3-infected MAE cells caused a significant inhibition of the mitogenic activity of the growth factor, whereas the conditioned media of s$C_{term}$-PTX3-infected and EGFP-infected MAE cells were ineffective (FIG. 1C). None of the conditioned media caused a significant inhibition of GM7373 cell proliferation triggered by 10% FCS, thus confirming the specificity of the effect.

Figure 2:
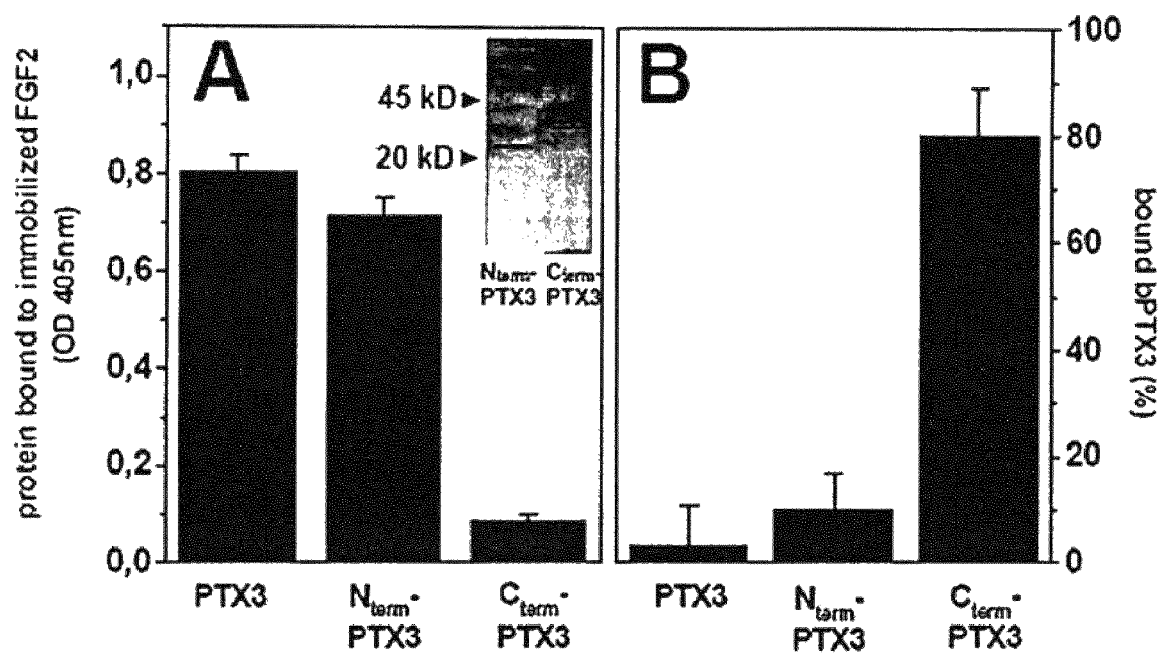
FIG. 2. Inhibition of FGF2/PTX3 interaction by recombinant $N_{term}$-PTX3. (A) Recombinant 6×His-tagged $N_{term}$-PTX3 and $C_{term}$-PTX3 were expressed and purified from transformed *E. coli* cells (inset shows the silver staining of a SDS-PAGE gel loaded with the purified proteins). Then, FGF2-coated wells were incubated with full length PTX3, $N_{term}$-PTX3 or $C_{term}$-PTX3 (all at 44 nM) for 30 minutes at 37° C. The relative amount of protein bound to immobilized FGF2 was immunodetected by incubation with a rabbit polyclonal anti-PTX3 antibody as described in Material and Methods. (B) FGF2-coated wells were incubated with biotinylated PTX3 (bPTX3, 22 nM) in the absence or in the presence of a 10 fold-molar excess of full length PTX3, $N_{term}$-PTX3 or $C_{term}$-PTX3. The amount of bPTX3 bound to immobilized FGF2 was then measured and data were expressed as percentage of binding measured in the absence of any competitor. All data are the mean±SD of 3 independent experiments in triplicate.

To confirm that the FGF2-antagonist activity of $N_{term}$-PTX3 was due to its capacity to interact directly with the growth factor, $N_{term}$-PTX3 was expressed and purified from transformed *E. coli* cells as a recombinant 6×His-tagged protein; purified recombinant 6×His-tagged $C_{term}$-PTX3 was used as a control (FIG. 2A, inset). When assessed for FGF2 interaction, full length PTX3 and the recombinant $N_{term}$-PTX3 fragment showed the capacity to bind FGF2 immobilized to non-tissue culture plastic. No interaction was instead observed with recombinant $C_{term}$-PTX3 (FIG. 2A). Accordingly, a 10 fold-molar excess of recombinant $N_{term}$-PTX3 or of full length PTX3, but not of $C_{term}$-PTX3, prevented the binding of biotinylated PTX3 (bPTX3) to immobilized FGF2 (FIG. 2B).

Taken together, these results implicate the N-terminal region of PTX3 for FGF2 interaction.

Figure 3:
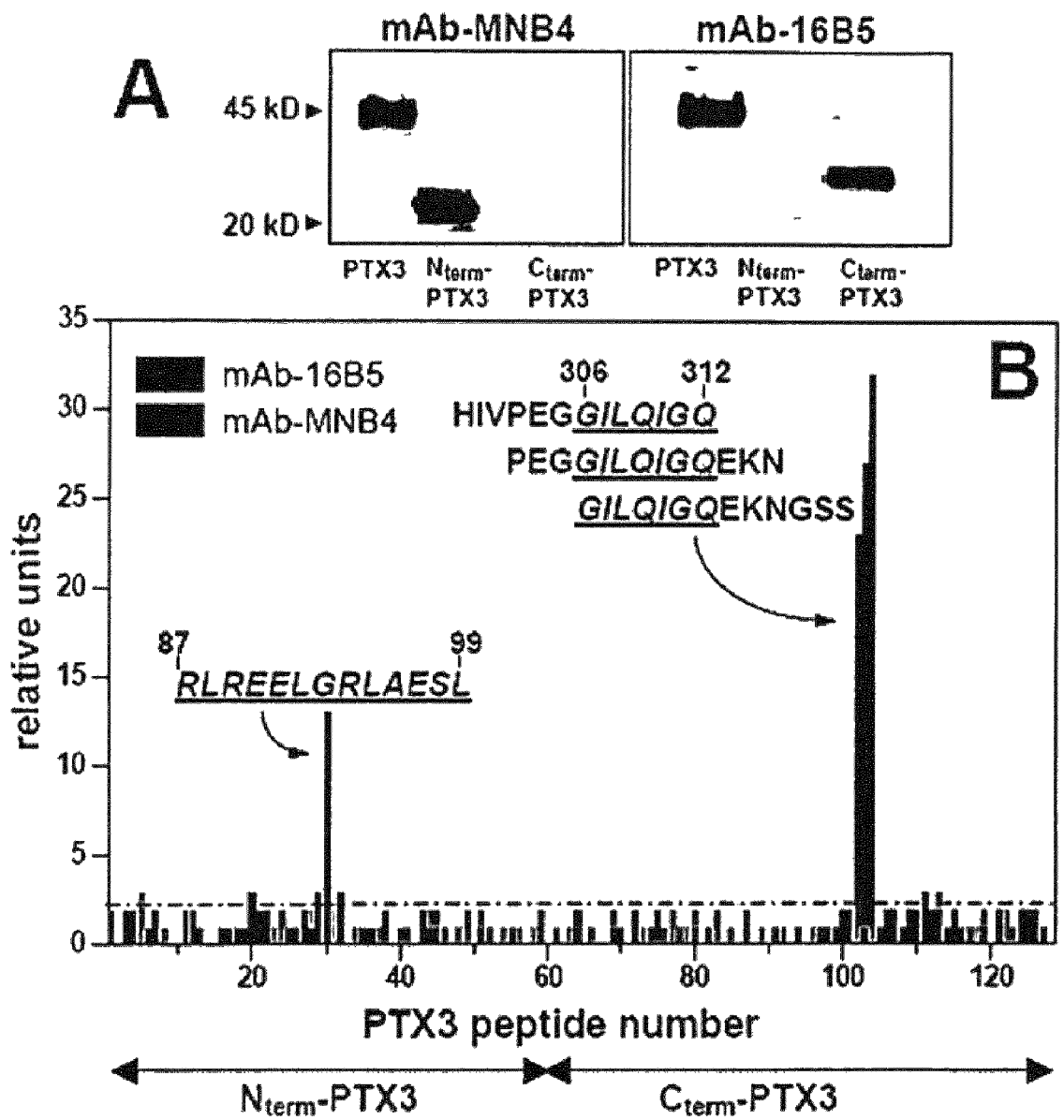
FIG. 3. PTX3 epitope mapping. (A) Full length PTX3, $N_{term}$-PTX3, and $C_{term}$PTX3 (200 ng/lane) were analyzed by Western blotting using the monoclonal antibodies mAb- MNB4 and mAb-16B5. (B) 128 overlapping 13-mer peptides spanning the entire human PTX3 sequence were arrayed on cellulose membranes by the SPOT-synthesis technique. Then, membranes were probed with mAb-15 MNB4 (black bars) and mAb-16B5 (gray bars) antibodies and immuno-complexes were quantified by densitometric analysis of the membranes. The amino acid sequence of the PTX3 peptides SEQ ID NO: 22 to SEQ ID NO: 25 recognized by the two antibodies are shown in underlined italic in the single letter code.

Inhibition of FGF2/PTX3 Interaction by a Monoclonal Anti-$N_{term}$-PTX3 Antibody The screening of a set of rat monoclonal antibodies raised against human full length PTX3 identified the antibodies mAb-MNB4[20] (MNB4 cat. Number ALX-804-464, Alexis Biochemicals) and mAb-16B5[10] (MNB1 cat. Number ALX-804-463, Alexis Biochemicals) that selectively bind recombinant $N_{term}$-PTX3 and $C_{term}$-PTX3, respectively, in a Western blot (FIG. 3A).

To map the PTX3 epitopes recognized by the two antibodies, the authors took advantage of the SPOT-synthesis technique[23] by which 128 overlapping 13-mer peptides spanning the entire human PTX3 sequence were arrayed on a cellulose membrane. When the membrane was probed with the two monoclonal antibodies, immunocomplex detection revealed that mAb-MNB4 recognizes the epitope PTX3(87-99) present in the N-terminal extension of PTX3 whereas mAb-16B5 recognizes the epitope PTX3(306-312) located in the C-terminal region of PTX3 (FIG. 3B).

Figure 4:
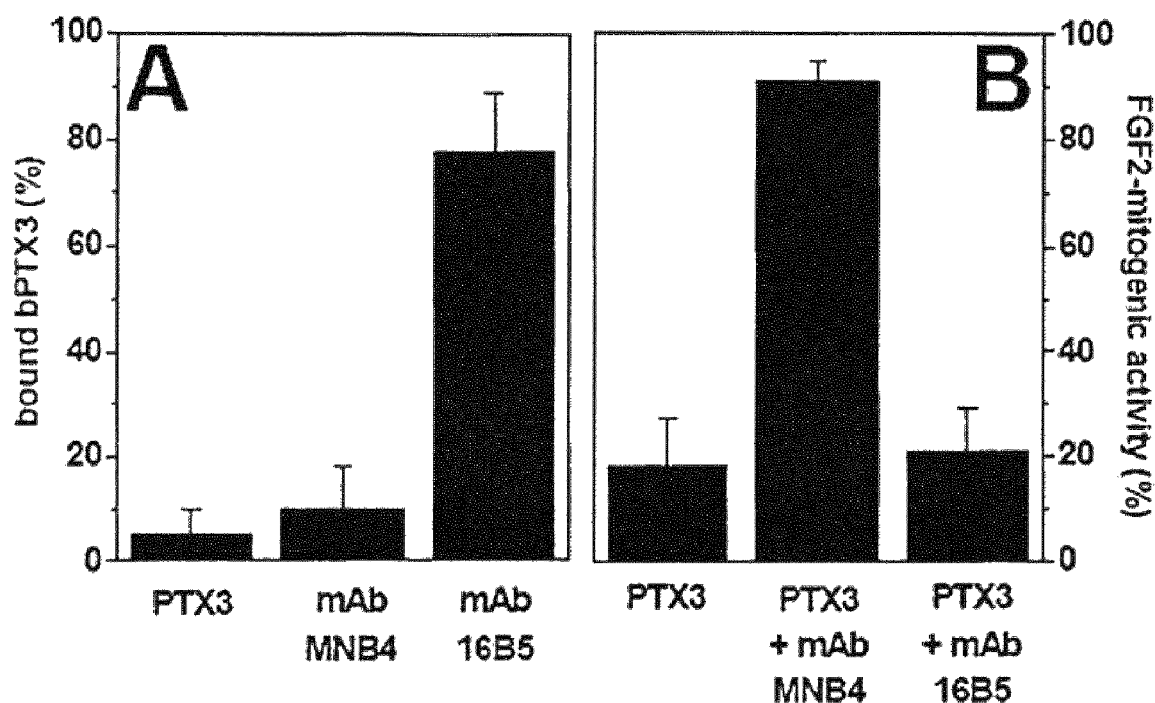
FIG. 4. mAb-MNB4 hampers FGF2/PTX3 interaction. (A) FGF2-coated wells were incubated with 22 nM bPTX3 in the absence or in the presence of full length PTX3, mAb-MNB4, or mAb-16B5 (all at 220 nM). The amount of bPTX3 bound to immobilized FGF2 was then measured and data were expressed as percentage of binding measured in the absence of any competitor. (B) GM7373 cells were incubated with FGF2 (0.55 nM) plus PTX3 (220 nM) in the absence or in the presence of mAb-MNB4 or mAb-16B5 (both at 2.2 µM). After 24 h, cells were trypsinized and counted. Data are expressed as percentage of the proliferation observed in GM7373 cells incubated with FGF2 only. All data are the mean±SD of 3 independent experiments in triplicate.

When tested for the capacity to affect FGF2/PTX3 interaction, mAb-MNB4, but not mAb-16B5, prevents the capacity of bPTX3 to bind immobilized FGF2, similar to a molar excess of free unlabeled PTX3 (FIG. 4A). Accordingly, mAb-MNB4 abolishes the capacity of full length PTX3 to inhibit the mitogenic activity exerted by FGF2 in endothelial GM7373 cells whereas mAb-16B5 is ineffective (FIG. 4B). Thus, mAb-MNB4 recognizing the N-terminal PTX3(87-99) epitope neutralizes FGF2/PTX3 interaction.

Synthetic $N_{term}$-PTX3-related Peptides as FGF2 Antagonists

Figure 5:
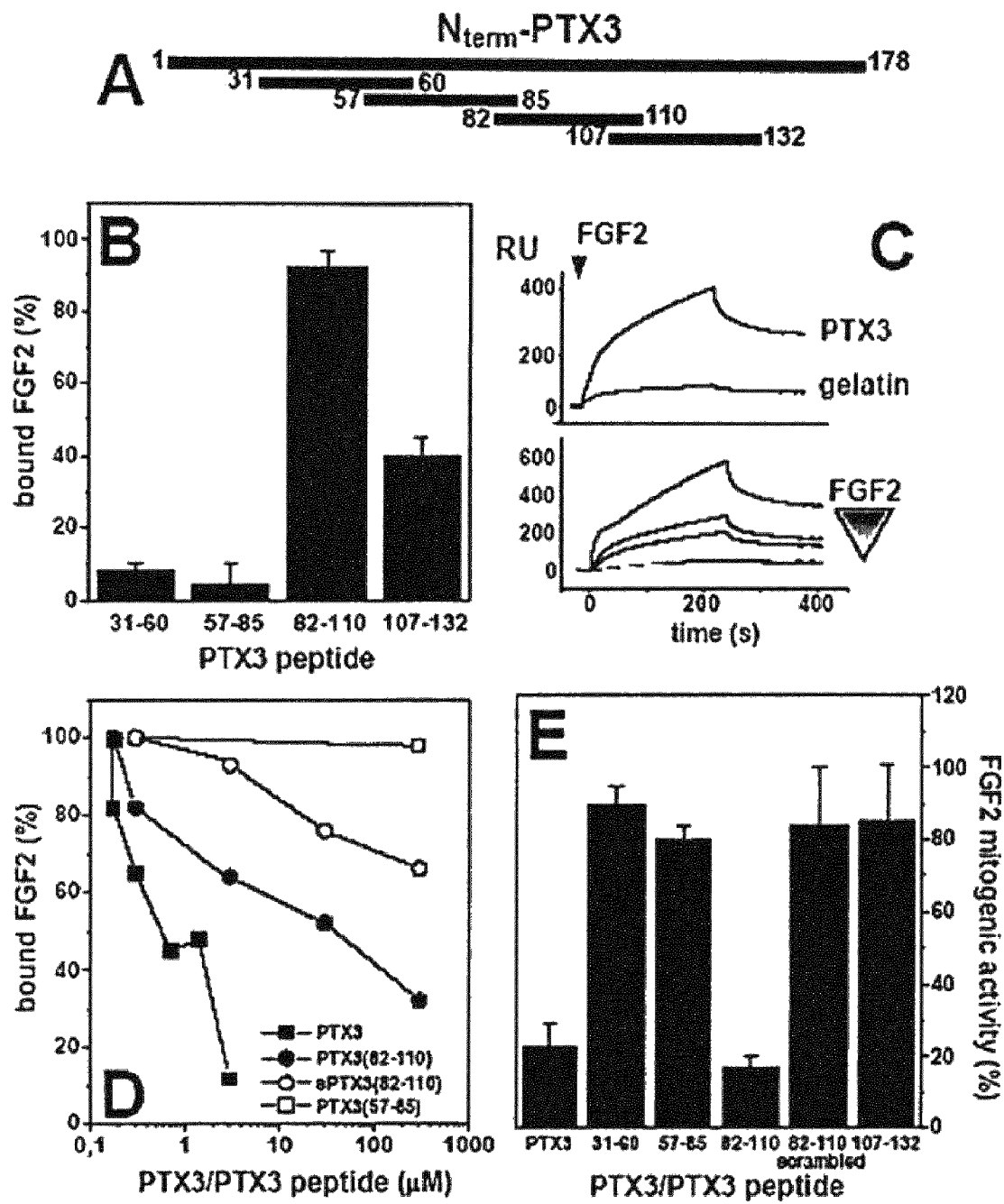
FIG. 5. Inhibition of FGF2/PTX3 interaction by synthetic PTX3 peptides. (A) Schematic representation of human PTX3 N-terminus and related synthetic PTX3 peptides. (B) Wells coated with the indicated PTX3 peptides (200 µg/well) were added with FGF2 (80 nM) and the amount of FGF2 bound was evaluated. Data, expressed as percentage of the amount of FGF2 bound to PTX3-coated wells, are the mean±SD of 3 independent experiments in triplicate. (C) Upper panel: FGF2 (0.8 µM) was injected over PTX3-coated or gelatin-coated BIAcore sensorchips. Lower panel: sensogram overlay showing the binding of increasing amounts of FGF2 (0.1, 0.5, 0.8, and 1.1 µM) to immobilized PTX3. The response (in RU, Resonance Units) was recorded as a function of time. D) FGF2 (0.8 µM) was injected over a PTX3-coated BIAcore sensorchip in the presence of increasing concentrations of full length PTX3 (■) or synthetic peptides PTX3(82-110) (●), scrambled PTX3(82-110) (○), or PTX3 (57-85) (□). The response was recorded at the end of injection and plotted as a function of the antagonist concentration. For each peptide, similar results were obtained in 2-3 independent experiments. (E) GM7373 cells were incubated with FGF2 (0.55 nM) in the absence or in the presence of PTX3 (220 nM) or of the indicated PTX3 peptides (all at 66 µM). Data, expressed as percentage of the proliferation observed in GM7373 cells incubated with FGF2 only, are the mean±SD of 3 independent experiments in triplicate.

To further define the FGF2-binding region in the N-terminal extension of PTX3, the authors evaluated the FGF2-antagonist activity of the synthetic peptide PTX3(82-110), that contains the PTX3(87-99) epitope recognized by the neutralizing mAb-MNB4 (see above), together with three distinct synthetic peptides PTX3(31-60), PTX3(57-85), and PTX3 (107-132) partially spanning the $N_{term}$-PTX3 amino acid sequence (FIG. 5A).

In a first set of experiments, the four synthetic PTX3 fragments were assessed for their capacity to interact with FGF2 in a solid phase binding assay. As shown in FIG. 5B, free FGF2 binds to PTX3(82-110) immobilized onto non-tissue culture plastic but not to immobilized PTX3(31-60) or PTX3 (57-85), showing only a limited interaction with immobilized PTX3(107-132).

Next, surface plasmon resonance was exploited to assess the ability of the four peptides to affect FGF2/PTX3 interaction. Results show that FGF2 (0.8 µM) binds to PTX3 immobilized to a BIAcore sensorchip with high capacity (350-400 RU bound at the end of the injection phase) (FIG. 5C, upper panel). Specificity of the interaction is demonstrated by the lack of binding to a gelatin-coated sensorchip. Also, increasing concentrations of FGF2 (from 0.1 to 1.1 µM, FIG. 5C, lower panel) were injected over the PTX3 surface to evaluate the kinetic parameters of FGF2/PTX3 interaction. The binding data demonstrate that the interaction occurs with a kinetic dissociation constant ($k_{off}$) of $6 \times 10^{-5}$ s$^{-1}$ and a kinetic association constant ($k_{on}$) of $0.2 \times 10$ s$^{-1}$ M$^{-1}$, thus resulting in a $K_d$ value equal to $0.3 \times 10^{-6}$ M$^{-1}$. On this basis, the four synthetic PTX3 peptides were assessed for their capacity to sequester FGF2 in the mobile phase, thus preventing its interaction with the PTX3 sensorchip. As shown in FIG. 5D, PTX3(82-110) inhibits the binding of FGF2 to the PTX3 surface in a dose-dependent manner with a potency 30 times lower than that shown by free full length PTX3 ($ID_{50}$ equal to 1.0 µM and 30 µM for free PTX3 and PTX3(82-110) peptide, respectively). Under the same experimental conditions, no inhibitory effect was instead exerted by PTX3(31-60), PTX3(57-85), and PTX3(107-132) peptides (FIG. 5D and other collected data). Also, a scrambled synthetic peptide with amino acid composition equal to PTX3(82-110) [sPTX3(82-110), Table 1] showed a limited inhibitory effect ($ID_{50}$>3000 µM) (FIG. 5D), thus indicating that the primary amino acid sequence in PTX3(82-110) is of importance for FGF2 interaction.

The capacity of PTX3(82-110) peptide to bind FGF2 prompted the authors to assess its ability to act as a FGF2-antagonist. When tested on endothelial GM7373 cells, both full length PTX3 and PTX3(82-110) inhibit the mitogenic activity exerted by exogenous FGF2, whereas scrambled PTX3(82-110), PTX3(31-60), PTX3(57-85), and PTX3 (107-132) peptides were ineffective (FIG. 5E). Dose-response curves confirmed that the FGF2-antagonist activity of PTX3(82-110) was dose-dependent ($ID_{50}$ equal 30 µM and 30 nM for PTX3(82-110) and PTX3, respectively).

Identification of a Minimal Linear FGF2-Binding Sequence in the N-Terminal Extension of PTX3

Figure 6:
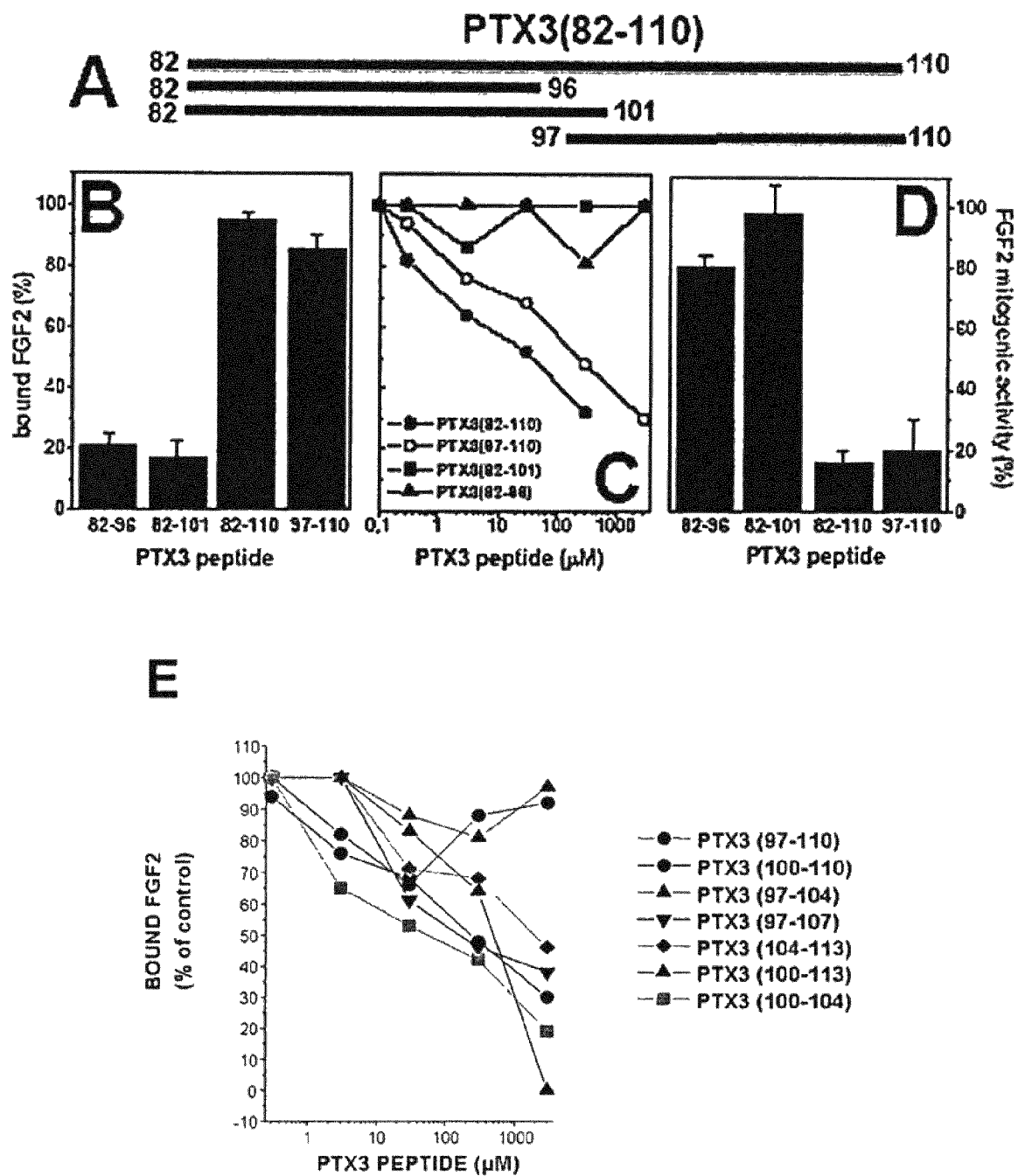
FIG. 6. PTX3(97-110) peptide as a FGF2 antagonist. (A) Schematic representation of PTX3(82-110) spanning peptides. (B) Wells coated with the indicated PTX3 peptides (200 µg/well) were incubated with FGF2 (80 nM) and the amount of bound FGF2 was evaluated. Data, expressed as percentage of the amount of FGF2 bound to PTX3-coated wells, are the mean±SD of 3 independent experiments in triplicate. (C) FGF2 (0.8 µM) was injected over a PTX3-coated BIAcore sensorchip in the presence of increasing concentrations of PTX3(82-110) (●), PTX3(97-110) (○), PTX3(82-101) (■), or PTX3(82-96) (▲). The response was recorded at the end of injection and plotted as a function of the antagonist concentration. For each peptide, similar results were obtained in 2-3 independent experiments. (D) GM7373 cells were incubated with FGF2 (0.55 nM) in the absence or in the presence of the indicated PTX3 peptides (all at 66 µM). Data, expressed as percentage of the proliferation observed in GM7373 cells incubated with FGF2 only, are the mean±SD of 3 independent experiments in triplicate. (E) FGF2 (0.8 µM) was injected over a PTX3-coated BIAcore sensorchip in the presence of increasing concentrations of PTX3(97-110) (●), PTX3(100-110) (○), PTX3(97-104) (▲), or PTX3(97-107) (▼), PTX3 (104-113) (♦), PTX3(100-113) (▲), PTX3(100-104) (■). The response was recorded at the end of injection and plotted as a function of the antagonist concentration. For each peptide, similar results were obtained in 2-3 independent experiments.

Taken together, the above data indicate that the linear amino acid sequence 82-110 in the N-terminal extension of PTX3 plays an important role in FGF2 interaction. In the attempt to identify a minimal linear FGF2-binding sequence, three overlapping synthetic peptides PTX3(82-96), PTX3 (82-101), and PTX3(97-110) spanning the entire PTX3(82-110) sequence (FIG. 6A and Table 1) were evaluated for the capacity to interact with FGF2 in a solid phase binding assay. Under the same experimental conditions, free FGF2 binds to immobilized PTX3(97-110), as well as to parental PTX3(82-110) and full length PTX3, without interacting with PTX3 (82-96) or PTX3(82-101) (FIG. 6B). Accordingly, PTX3(97-110) binds FGF2 in the mobile phase, thus preventing its interaction with PTX3 immobilized to a BIAcore sensorchip (FIG. 6C). The inhibitory activity of PTX3(97-110) was similar to that shown by the parental peptide PTX3(82-110), whereas PTX3(82-96) and PTX3(82-101) were ineffective (FIG. 6C). In keeping with these observations, PTX3(97-110), but not PTX3(82-96) or PTX3(82-101), inhibits the mitogenic activity exerted by FGF2 in endothelial GM7373 cells (FIG. 6D).

To further investigate the minimal linear FGF2-binding sequence spanning the peptide PTX3(97-110), the authors analysed the binding of the following shorter peptides to FGF2 by measuring its interaction with PTX3 immobilized to a BIAcore sensorchip: PTX3(97-107), PTX3(97-104), PTX3 (100-104) and PTX3(100-110), (FIG. 6E). Peptides PTX3 (97-107) and PTX3(100-104) showed a significant binding to FGF2. In contrast peptides PTX3(97-104) and PTX3(100-110) did not prevent the binding of free FGF2 to PTX3 immobilized to a BIAcore sensorchip. (FIG. 6E). Thus, PTX3 (100-104) appears to represent the minimal linear FGF2-binding amino acid sequence in the N-terminal extension of PTX3. Accordingly, PTX3(100-104) inhibits FGF2-induced endothelial cell proliferation.

Synthetic $N_{term}$-PTX3-related Peptides Inhibit the Angiogenic Activity of FGF2

Figure 7:
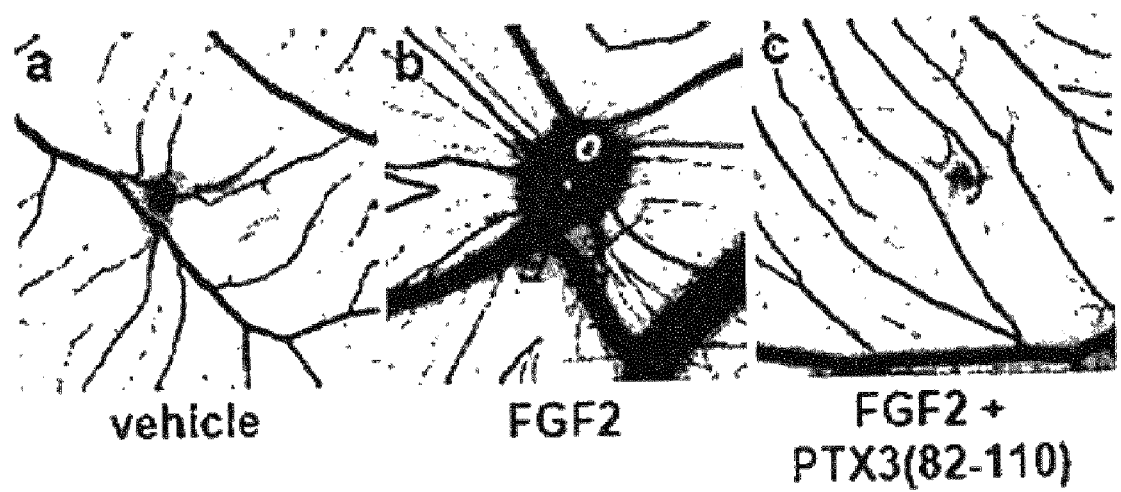
FIG. 7. Anti-angiogenic activity of PTX3(82-110) peptide. Chicken embryo chorioallantoic membrane (CAM) implanted at day 11 with alginate beads containing vehicle (a) or 16 pmoles FGF2 in the absence (b) or in the presence (c) of 3 nmoles of PTX3(82-110) were photographed at day 14. Original magnification, ×5.

To assess the capacity of $N_{term}$-PTX3-related peptides to affect FGF2-induced neovascularization in vivo, gelatin sponges adsorbed with FGF2 alone or added with PTX3 peptides were implanted on the top of 11 day-old chick embryo CAMs. As shown in FIG. 7, alginate beads adsorbed with FGF2 (16 pmoles/embryo) exert a potent angiogenic response when compared to beads adsorbed with vehicle (macroscopic vessels converging towards the implant being equal to 44±7 and 11±5 vessels/embryo for the two experimental groups, respectively). In keeping with the in vitro observations, the in vivo FGF2-dependent angiogenic response was significantly reduced (28±5 vessels/embryo, p<0.05 by ANOVA) by the addition of 3.0 nmoles of PTX3 (82-110) peptide in the FGF2 implants (FIG. 7). Accordingly, 80 nmoles of PTX3(97-110) caused a 50% inhibition in the angiogenic response triggered by FGF2; no effect was instead exerted by PTX3(82-96).

Discussion

The authors show that FGF2 interaction is mediated by the N-terminal extension on PTX3. Also, experiments performed with neutralizing monoclonal antibodies and synthetic PTX3-related peptides identify the amino acid linear sequence PTX3(97-110) as responsible for this interaction. These conclusions are based on the following experimental evidences: i) the short-pentraxins CRP and SAP are inefficient FGF2 binders[17] despite their sequence homology with the PTX3 C-terminus[7]; ii) retroviral transduction of the N-terminal fragment PTX3(1-178) ($N_{term}$-PTX3), but not of $sC_{term}$-PTX3, inhibits the mitogenic activity exerted by exogenous FGF2 in endothelial cells; iii) recombinant $N_{term}$-PTX3, but not $C_{term}$-PTX3, binds to immobilized FGF2 and inhibits PTX3/FGF2 interaction; iv) the monoclonal antibody mAb-MNB4, mapping the linear epitope PTX3(87-99), prevents FGF2/PTX3 interaction and abolishes the FGF2 antagonist activity of PTX3 in endothelial cells; v) the synthetic peptide PTX3(82-110) and the shorter peptides PTX3 (97-110), PTX3(97-107) and PTX3(100-104), but not other peptides based on different regions of the PTX3 N-terminus, prevent FGF2/PTX3 interaction by binding FGF2, thus inhibiting FGF2-dependent endothelial cell proliferation in vitro and angiogenesis in vivo.

PTX3 is produced by macrophages[27], fibroblasts[9], myoblasts[28], microglia[29], and endothelial cells[8], indicating that it may exert paracrine and autocrine functions on endothelium. Similarly, various stimuli, including the inflammatory mediators IL-1 and nitric oxide[30,31] induce FGF2 expression in endothelial cells that undergo an autocrine loop of stimulation. Thus, endothelial cells and other cell types can express both PTX3 and FGF2. Thus, PTX3 produced by inflammatory cells or by endothelial cells themselves may affect the autocrine and paracrine activity exerted by FGF2 on endothelium in vitro and in vivo. This should allow a fine tuning of neovascularization via the production of both angiogenesis inhibitors and stimulators.

FGF2 is a pleiotropic growth factor that stimulates various cell types of endodermal and mesodermal origin[32]. Therefore, the role exerted by FGF2 in various pathophysiological conditions is not limited to its angiogenic activity. For instance, FGF2 stimulates the migration and proliferation of fibroblasts during wound healing and of smooth muscle cells during atherosclerosis[33,34] and restenosis[35]. Also, it may favor neuronal cell survival and glia cell proliferation in the injured central nervous system[36]. In all these conditions, the concomitant production of PTX3[37,38] modulate the activity exerted by FGF2 on these cells. Indeed, PTX3 inhibits FGF2-dependent smooth muscle cell activation in vitro and intimal thickening after arterial injury in vivo[18].

In conclusion, the authors demonstrate for the first time that PTX3 N-terminus is involved in FGF2 interaction. PTX3 is a multifunctional soluble pattern recognition receptor at the crossroads between innate immunity, inflammation, matrix deposition, and female fertility. It exerts its multifunctional activity by interacting with numerous ligands with distinct molecular properties.

Further, the hard copy of the sequence listing submitted herewith and the corresponding computer readable form are both incorporated herein by reference in their entirety.

REFERENCES

1. Garlanda C, Bottazzi B, Bastone A, Mantovani A. Pentraxins at the crossroads between innate immunity, inflammation, matrix deposition, and female fertility. Annu Rev Immunol. 2005; 23:337-366
2. Steel D M, Whitehead A S. The major acute phase reactants: C-reactive protein, serum amyloid P component and serum amyloid A protein. Immunol Today. 1994; 15:81-88
3. Pepys M B, Baltz M L. Acute phase proteins with special reference to C-reactive protein and related proteins (pentaxins) and serum amyloid A protein. Adv Immunol. 1983; 34:141-212
4. Du Clos T W. The interaction of C-reactive protein and serum amyloid P component with nuclear antigens. Mol Biol Rep. 1996; 23:253-260
5. Gewurz H, Zhang X H, Lint T F. Structure and function of the pentraxins. Curr Opin Immunol. 1995; 7:54-64
6. Nauta A J, Daha M R, van Kooten C, Roos A. Recognition and clearance of apoptotic cells: a role for complement and pentraxins. Trends Immunol. 2003; 24:148-154
7. Goodman A R, Cardozo T, Abagyan R, Altmeyer A, Wisniewski H G, Vilcek J. Long pentraxins: an emerging group of proteins with diverse functions. Cytokine Growth Factor Rev. 1996; 7:191-202
8. Breviario F, d'Aniello E M, Golay J, Peri G, Bottazzi B, Bairoch A, Saccone S, Marzella R, Predazzi V, Rocchi M, et al. Interleukin-1-inducible genes in endothelial cells. Cloning of a new gene related to C-reactive protein and serum amyloid P component. J Biol. Chem. 1992; 267: 22190-22197
9. Lee G W, Lee T H, Vilcek J. TSG-14, a tumor necrosis factor- and IL-1-inducible protein, is a novel member of the pentaxin family of acute phase proteins. J. Immunol. 1993; 150:1804-1812
10. Boftazzi B, Vouret-Craviari V, Bastone A, De Gioia L, Matteucci C, Peri G, Spreafico F, Pausa M, D'Ettorre C, Gianazza E, Tagliabue A, Salmona M, Tedesco F, Introna M, Mantovani A. Multimer formation and ligand recognition by the long pentraxin PTX3. Similarities and differences with the short pentraxins C-reactive protein and serum amyloid P component. J Biol. Chem. 1997; 272: 32817-32823
11. Basile A, Sica A, d'Aniello E, Breviario F, Gamido G, Castellano M, Mantovani A, Introna M. Characterization of the promoter for the human long pentraxin PTX3. Role of NF-kappaB in tumor necrosis factor-alpha and interleukin-1 beta regulation. J Biol Chem. 1997; 272:8172-8178
12. Salustri A, Garlanda C, Hirsch E, De Acetis M, Maccagno A, Bottazzi B, Doni A, Bastone A, Mantovani G, Beck Peccoz P, Salvatori G, Mahoney D J, Day A J, Siracusa G, Romani L, Mantovani A. PTX3 plays a key role in the organization of the cumulus oophorus extracellular matrix and in in vivo fertilization. Development. 2004; 131:1577-1586
13. Garlanda C, Hirsch E, Bozza S, Salustri A, De Acetis M, Nota R, Maccagno A, Riva F, Bottazzi B, Peri G, Doni A, Vago L, Botto M, De Santis R, Carminati P, Siracusa G, Altruda F, Vecchi A, Romani L, Mantovani A. Non-redundant role of the long pentraxin PTX3 in anti-fungal innate immune response. Nature. 2002; 420:182-186
14. Mantovani A, Garlanda C, Bottazzi B. Pentraxin 3, a non-redundant soluble pattern recognition receptor involved in innate immunity. Vaccine. 2003; 21 Suppl 2:S43-47
15. Gerwins P, Skoldenberg E, Claesson-Welsh L. Function of fibroblast growth factors and vascular endothelial growth factors and their receptors in angiogenesis. Crit. Rev. Oncol. Hematol. 2000; 34:185-194
16. Presta M, Dell'Era P, Mitola S, Moroni E, Ronca R, Rusnati M. Fibroblast growth factor/fibroblast growth factor receptor system in angiogenesis. Cytokine Growth Factor Rev. 2005; 16:159-178
17. Rusnati M, Camozzi M, Moroni E, Bottazzi B, Peri G, Indraccolo S, Amadori A, Mantovani A, Presta M. Selective recognition of fibroblast growth factor-2 by the long pentraxin PTX3 inhibits angiogenesis. Blood. 2004; 104: 92-99
18. Camozzi M, Zacchigna S, Rusnati M, Coltrini D, Ramirez-Correa G, Bottazzi B, Mantovani A, Giacca M, Presta M. Pentraxin 3 inhibits fibroblast growth factor 2-dependent activation of smooth muscle cells in vitro and neointima formation in vivo. Arterioscler Thromb Vasc Biol. 2005; 25:1837-1842
19. Isacchi A, Statuto M, Chiesa R, Bergonzoni L, Rusnati M, Sarmientos P, Ragnotti G, Presta M. A six-amino acid deletion in basic fibroblast growth factor dissociates its mitogenic activity from its plasminogen activator-inducing capacity. Proc Natl Acad Sci USA. 1991; 88:2628-2632
20. Peri G, Introna M, Corradi D, Iacuitti G, Signorini S, Avanzini F, Pizzetti F, Maggioni A P, Moccetti T, Metra M, Cas L D, Ghezzi P, Sipe J D, Re G, Olivetti G, Mantovani A, Latini R. PTX3, A prototypical long pentraxin, is an early indicator of acute myocardial infarction in humans. Circulation. 2000; 102:636-641
21. Grinspan J B, Mueller S N, Levine E M. Bovine endothelial cells transformed in vitro by benzo(a)pyrene. J Cell Physiol. 1983; 114:328-338
22. Presta M, Maier J A, Rusnati M, Ragnotti G. Basic fibroblast growth factor: production, mitogenic response, and post-receptor signal transduction in cultured normal and transformed fetal bovine aortic endothelial cells. J Cell Physiol. 1989; 141:517-526
23. Frank R, Overwin H. SPOT synthesis. Epitope analysis with arrays of synthetic peptides prepared on cellulose membranes. Methods Mol. Biol. 1996; 66:149-169
24. Knoll A, Schmidt S, Chapman M, Wiley D, Bulgrin J, Blank J, Kirchner L. A comparison of two controlled-release delivery systems for the delivery of amiloride to control angiogenesis. Microvasc Res. 1999; 58:1-9
25. Emsley J, White H E, O'Hara B P, Oliva G, Srinivasan N, Tickle I J, Blundell T L, Pepys M B, Wood S P. Structure of pentameric human serum amyloid P component. Nature. 1994; 367:338-345
26. Eriksson A E, Cousens L S, Weaver L H, Matthews B W. Three-dimensional structure of human basic fibroblast growth factor. Proc. Natl. Acad. Sci. U.S.A. 1991; 88:3441-3445
27. Vouret-Craviari V, Matteucci C, Peri G, Poli G, Introna M, Mantovani A. Expression of a long pentraxin, PTX3, by monocytes exposed to the mycobacterial cell wall component lipoarabinomannan. Infect Immun. 1997; 65:1345-1350
28. Introna M, Alles W, Castellano M, Picardi G, De Gioia L, Bottazzai B, Peri G, Breviario F, Salmona M, De Gregorio L, Dragani T A, Srinivasan N, Blundell T L, Hamilton T A, Mantovani A. Cloning of mouse ptx3, a new member of the pentraxin gene family expressed at extrahepatic sites. Blood. 1996; 87:1862-1872

29. Polentarutti N, Bottazzi B, Di Santo E, Blasi E, Agnello D, Ghezzi P, Introna M, Bartfai T, Richards G, Mantovani A. Inducible expression of the long pentraxin PTX3 in the central nervous system. J. Neuroimmunol. 2000; 106:87-94

30. Samaniego F, Markham P D, Gendelman R, Gallo R C, Ensoli B. Inflammatory cytokines induce endothelial cells to produce and release basic fibroblast growth factor and to promote Kaposi's sarcoma-like lesions in nude mice. J. Immunol. 1997; 158:1887-1894

31. Ziche M, Parenti A, Ledda F, Dell'Era P, Granger H J, Maggi C A, Presta M. Nitric oxide promotes proliferation and plasminogen activator production by coronary venular endothelium through endogenous bFGF. Circ Res. 1997; 80:845-852

32. Rifkin D B, Moscatelli D. Recent developments in the cell biology of basic fibroblast growth factor. J. Cell Biol. 1989; 109:1-6

33. Blotnick S, Peoples G E, Freeman M R, Eberlein T J, Klagsbrun M. T lymphocytes synthesize and export heparin-binding epidermal growth factor-like growth factor and basic fibroblast growth factor, mitogens for vascular cells and fibroblasts: differential production and release by CD4+ and CD8+ T cells. Proc Natl Acad Sci USA. 1994; 91:2890-2894

34. Peoples G E, Blotnick S, Takahashi K, Freeman M R, Klagsbrun M, Eberlein T J. T lymphocytes that infiltrate tumors and atherosclerotic plaques produce heparin-binding epidermal growth factor-like growth factor and basic fibroblast growth factor: a potential pathologic role. Proc Natl Acad Sci USA. 1995; 92:6547-6551

35. Reidy M A, Fingerle J, Lindner V. Factors controlling the development of arterial lesions after injury. Circulation. 1992; 86:11143-46

36. Logan A, Berry M. Transforming growth factor-beta 1 and basic fibroblast growth factor in the injured CNS. Trends Pharmacol Sci. 1993; 14:337-342

37. Ravizza T, Moneta D, Bottazzi B, Peri G, Garlanda C, Hirsch E, Richards G J, Mantovani A, Vezzani A. Dynamic induction of the long pentraxin PTX3 in the CNS after limbic seizures: evidence for a protective role in seizure-induced neurodegeneration. Neuroscience. 2001; 105:43-53

38. Rolph M S, Zimmer S, Bottazzi B, Garlanda C, Mantovani A, Hansson G K. Production of the long pentraxin PTX3 in advanced atherosclerotic plaques. Arterioscler Thromb Vasc Biol. 2002; 22:e10-14

The invention claimed is:

1. An FGF-2 binding peptide wherein the peptide consists of an amino acid sequence selected from the group consisting of SEQ ID NO: 5, SEQ ID NO: 6, SEQ ID NO: 7, and SEQ ID NO: 10 or a pharmaceutically acceptable salt thereof.

2. A pharmaceutical composition comprising the FGF-2 binding peptide of claim 1 or pharmaceutically acceptable salt thereof and a pharmaceutically acceptable carrier, diluent, excipient, and/or adjuvant.

3. A fused peptide comprising the FGF-2 binding peptide according to claim 1 fused to a protein sequence other than a human PTX3 amino acid sequence, the protein selected from the group consisting of membrane-bound proteins, extracellular regions of membrane-bound proteins, immunoglobulin constant regions, multimerization domains, extracellular proteins, signal peptide-containing proteins, and export signal-containing proteins.

4. A conjugated peptide comprising the FGF-2 binding peptide of claim 1 conjugated to a heterologous moiety.

* * * * *